United States Patent [19]

Lonsbury-Martin et al.

[11] Patent Number: 5,664,577

[45] Date of Patent: Sep. 9, 1997

[54] METHOD AND APPARATUS FOR DISTORTION PRODUCT EMISSION TESTING OF HEARING

[75] Inventors: Brenda L. Lonsbury-Martin; Glen K. Martin, both of Houston, Tex.

[73] Assignee: Baylor College of Medicine, Houston, Tex.

[21] Appl. No.: 662,881

[22] Filed: Jun. 13, 1996

Related U.S. Application Data

[63] Continuation of Ser. No. 296,868, Aug. 26, 1994, Pat. No. 5,526,819, which is a continuation of Ser. No. 64,356, May 18, 1993, abandoned, which is a continuation of Ser. No. 471,106, Jan. 25, 1990, abandoned.

[51] Int. Cl.$^6$ .................................................. G06G 7/60
[52] U.S. Cl. .................................................. 128/746
[58] Field of Search .............................. 128/746; 73/585, 73/587, 801; 381/25, 23.1

[56] References Cited

U.S. PATENT DOCUMENTS

| | | | |
|---|---|---|---|
| 4,374,526 | 2/1983 | Kemp | 128/746 |
| 4,459,996 | 7/1984 | Teele | 128/746 |
| 4,589,137 | 5/1986 | Miller | 381/94 |
| 4,630,304 | 12/1986 | Borth et al. | 381/94 |
| 4,636,586 | 1/1987 | Schiff | 379/390 |
| 4,649,505 | 3/1987 | Zinser, Jr. et al. | 379/411 |
| 4,653,102 | 3/1987 | Hansen | 381/92 |
| 4,672,674 | 6/1987 | Clough et al. | 381/71 |
| 4,684,989 | 8/1987 | Roeder | 358/167 |
| 4,716,907 | 1/1988 | Nakamura | 128/731 |
| 4,884,447 | 12/1989 | Kemp et al. | 73/585 |
| 5,033,082 | 7/1991 | Eriksson et al. | 379/410 |
| 5,267,571 | 12/1993 | Zurek et al. | 128/746 |
| 5,526,819 | 6/1996 | Lonsbury-Martin et al. | 128/746 |

OTHER PUBLICATIONS

D.T. Kemp, Stimulated acoustic emissions from within the human auditory system. Journal of Acoustical Society of America; vol. 64; pp. 1386–1391; Nov. 1978.

D.T. Kemp, Evidence of Mechanical Nonlinearity and Frequency Selective Wave Amplification in the Cochlea; Archives of Otorhinolaryngology; vol. 224; pp. 37–45; 1979.

Kemp, Bray, Alexander, Brown; Acoustic Emission Cochleography –Practical Aspects; Scand Audial Suppl.; vol. 25; pp. 71–95; 1986.

Bray and Kemp, An advanced cochlear echo technique suitable for infant screening; British Journal of Audiology; vol. 21; pp. 91–204; 1987.

Harris, Lonsbury–Martin, Stagner, Coats, Martin; Acoustic distortion products in humans: Systematic changes in amplitude as function of $f_2/f_1$ ratio; J. Acoustic Society of America; vol. 85; pp. 220–229; exact date unknown, Jan. 1989 printed on copy of paper.

(List continued on next page.)

Primary Examiner—Gail O. Hayes
Assistant Examiner—Frantzy Poinvil
Attorney, Agent, or Firm—Bush, Riddle & Jackson, L.L.P.

[57] ABSTRACT

Apparatus and method for the recording of distortion product emission (DPE) levels in human beings. At least one microphone and a sound-delivery system is inserted in the external ear canal. Two primary tones $T_{f1}$, $T_{f2}$ are applied simultaneously to the ear. The cochlea of the inner ear produces a DPE tone which is sensed by the microphone. DPE levels are sensed as a function of input frequencies $f_1$ and $f_2$. Such DPE frequency is equal to $2f_1-f_2$. Such DPE frequencies are collected in 100 Hz step by adjusting $f_1$ and $f_2$ and maintaining a substantially constant ratio between $f_1$ and $f_2$. Two output forms are created: an DPE audiogram and a DPE input/output function. Noise picked up is reduced by averaging the DPE signals many times, yet causing each of the DPE signals that is averaged to be of the same phase a every other DPE signal. Random phase noise is reduced by the averaging process. Body noise may be reduced by using two microphones and applying the output of one such microphones to the plus input of a differential amplifier. The output of such amplifier results with the body noise signal substantially reduced, but with the DPE signal substantially unchanged.

3 Claims, 6 Drawing Sheets

OTHER PUBLICATIONS

Schmiedt, Acoustic Distortion in the ear canal, I. Cubic different tones: Effects of acute noise injury; J. Acoustic Society of America; vol. 79(5) pp. 1481–1490; May 1986 (date printed on publication).

Schmiedt et al, Ear–canal acoustic emissions as frequency –specific indication of cochlear function; J. Acoustic Society of America Supplement 1; vol. 72 p. 56; Fall, 1982.

Kemp and Brown; An Integrated View of Cochlear Mechanical Nonlinearities Observable from the Ear Canal; unknown publication, vol., page and date.

D.T. Kemp; Otoacoustic emission, traveling waves and cochlear mechanism; Hearing research (Elsevier Science Publishers B.V. (Biomedical Div.)); vol. 22; pp. 95–104; 1986.

Schmiedt; Acoustic injury and the physiology of hearing; J. Acoustic Society of America; vol. 76(5); pp. 1293–1317; Nov. 1984 (printed on pages).

Bray and Kemp, "An advanced cochlear echo technique suitable for infant screening", British Journal of Audiology, vol. 21; pp. 91–204; 1987.

Journal of Acoustical Society of America, vol. 78, Mo 5, Nov. 1985, Horner et al., "Distortion product Otoacoustic emissions in hearing–impaired Mutant Mice", (abstract only).

J. Otoloryngol, vol. 18, No. 7, 1989, Kimberly et al., "Distortion Product Emissions and Sensorineutral Hearing Loss" (Abstract Only).

Hear ros., Jan. 1984, vol. 13, No. 1, Brown et al., "Suppressibility of the 2f1–f2 Stimulated Acoustic Emissions in Gerbil and Man" (Abstract only).

D.T. Kemp, Stimulated acoustic emissions from within the human auditory system. Journal of Acoustical Society of America; vol. 64; pp. 1386–1391; Nov. 1978.

D.T. Kemp, "Evidence of Mechanical Nonlinearity and Frequency Selective Wave Amplification i the Cochlea; Archives of Otorhinolaryngology"; vol. 224; pp. 37–45; 1979.

METHOD AND APPARATUS FOR DISTORTION PRODUCT EMISSION TESTING OF HEARING

This application is a continuation of Ser. No. 08/296,868, filed Aug. 26, 1994, now U.S. Pat. No. 5,526,819 which is a continuation of Ser. No. 08/064,356 filed May 18, 1993 now abandoned which is a continuation of Ser. No. 07/471, 106 filed Jan. 25, 1990 now abandoned.

U.S. GOVERNMENT SUPPORT

The invention described and claimed herein resulted from work supported by U.S. government grants from the National Institutes of Health. The Government has certain right in the invention.

BACKGROUND

1. Field of the Invention

This invention relates in general to hearing testing of a human being. In particular, the invention relates to recording of distortion product emissions (DPEs) of human ears. Still more particularly, the invention relates to apparatus and methods for recording DPE audiograms and input/output functions and to the minimization of random noise in the presence of DPE.

2. Description of the Prior Art

Otoacoustic Emissions (OAEs), first described in 1978, represent acoustic energy presumed to be generated by stimulus-induced, motile activity of the outer hair cells of the Organ of Corti in the Cochlea of the inner ear of a human being and other mammals. It is believed that mechanical feedback of such outer hair cells into basilar membrane motion and their related cochlear-efferent endings are part of a biomechanical gain system that is responsible for the sharp tuning and high sensitivity associated with normal hearing.

Otoacoustic emissions (OAEs) may be classified generally as spontaneous emissions and "evoked" or stimulated emissions. Stimulated emissions can be further separated into three subclasses consisting of transiently evoked emissions (TEEs), stimulus-frequency emissions (SFEs), and distortion-product emissions (DPEs). Each type of stimulus [i.e., clicks (TEEs) or low-level, continuous pure tones (SFEs) or continuous, simultaneously applied, two-tone stimuli (DPEs)] generates evoked emissions. TEEs and SFEs have an appreciable latent or delayed time period with respect to stimulus onset. DPEs, have a nonlatent or instantaneous onset. Based on the response-latency distinction, it is believed that separate subcellular components of the outer hair cell support the generation of delayed versus instantaneous evoked OAEs. For example, the stimulus-induced movements of the stereocilia bundle likely generate the nonlatent DPEs, while the motile activity of the lateral regions of the hair-cell membrane likely produces the latent TEEs and SFEs.

D. T. Kemp proposed that a transient OAE could be a diagnostic tool in the examination of impaired hearing. Kemp, *Stimulated Acoustic Emissions from within the Human Auditory System*, J. Acoust. Soc. Am., Vol 64, No. 5, pp 1386–1391, November 1978. After Kemp's discoveries became known to the art of hearing research, a number of researchers investigated the status of stimulated OAEs in people with normal hearing and with hearing impairments. Early studies established that emissions are present in essentially all normally hearing individuals and that such emissions are reduced or eliminated in regions of sensorineural hearing loss. Moreover, it became apparent that, of the three types of stimulated emissions, SFEs could not be simply applied in practical settings, because they require the utilization of complex methods of analysis in order to separate them from the eliciting stimulus.

Of the remaining evoked-emission types, that is TEEs and DPEs, TEEs have received, by far, the most attention as potential clinical measures of cochlear function. The development of transiently evoked otoacoustic emissions (TEEs) has, in fact, reached an advanced level in that a computer-based commercial device is currently available to the audiologist: D. T. Kemp, et al., *Acoustic Emission Cochleography—Practical Aspects*, Scand Audial Suppl. 25, pp. 71–95, 1986; Peter Bray and David Kemp, *An Advanced Cochlear echo Technique Suitable for Infant Screening*, British Journal of Audiology, 1987, No. 21, pp. 191–204.

The form of a TEE from a given ear is subject to the invariable influence of fixed-frequency emissions that are unique to that ear. In the presence of idiosyncratic frequencies, including the spontaneous and stimulus-frequency otoacoustic emissions, as well as the TEEs themselves, cochlear function, at specific frequencies (e.g., audiometric-test frequencies), cannot be uniquely assessed. Consequently, TEE testing appears most useful as a screening device for estimating the absence or presence of reasonably normal hearing.

In contrast to the significant attention that TEEs have received as potential clinical indicators of outer hair-cell cochlea function, DPEs have not been extensively investigated as the basis of an objective test of hearing impairment.

3. Identification of Objects of the Invention

In view of the inherent problems of using TEEs and SFEs for hearing testing, it is a general object of the invention to provide method and apparatus for using DPEs as the basis of an objective hearing test, both for normal and hearing-impaired ears.

It is another object of this invention to provide a method and apparatus by which an ear may be tested, using DPEs, for hearing capability at any frequency between approximately one and eight kHz. In other words, it is an object of this invention to provide a method and apparatus for creating a DPE audiogram for a human being.

It is another object of this invention to provide a method and apparatus by which an objective measure of the hearing capability at a particular frequency varies as a function of stimulus level, so as to permit a complete evaluation of cochlear function at both threshold and suprathreshold levels of stimulation. In other words, it is an object of the invention to provide a method and apparatus for creating a DPE input/output function for a human being.

It is another object of this invention to provide a method and apparatus by which DPEs may be used to evaluate remaining outer hair-cell function in hearing impared human beings having a hearing loss up to 45–55 dB HL.

It is another object of this invention to provide noise reduction method and apparatus for reducing the noise signal which contaminates the measurement of the DPE, thereby providing a system which may be used in a noisy environment such as a doctor's clinic or other hearing screening facility.

SUMMARY OF THE INVENTION

To produce DPEs, two related pure tones are simultaneously presented to the ear. Such tones usually, (but not necessarily required) are of equal amplitude. The non-linear response to such tones, believed to occur in the cochlea of the inner ear, generate a lower amplitude tone in the ear. Such tone, believed to be produced by biomechanical elements of the cochlea, is at a frequency lower than the frequency $f_1$ or $f_2$ of the two input tones. Such DPE tone is at a frequency of $2f_1-f_2$, but its amplitude is considerably lower than the amplitude of the two input tones at frequencies $f_1$ and $f_2$.

This invention includes providing first and second tones of respective frequencies $f_1$ and $f_2$ to the ear canal of the outer ear. Such tones are provided to an eartip via earphones driven by a signal generator. Such eartip includes at least one microphone for sensing not only the two input tones at frequencies $f_1$ and $f_2$, but also the DPE tone at frequency $2f_1-f_2$. The microphone electrical signal output is amplified and then applied to a spectrum analyzer which produces, a signal output representative of the level of each frequency in the spectrum of frequencies of such microphone electrical signal output.

According to one aspect of the invention, a programmed digital computer controls the generation of the input tones and the recording of levels of the various frequencies received from the microphone electrical signal output of the spectrum analyzer. Over a frequency range such as 1 kHz to 8 kHz, input tones are generated and responses recorded by the frequency analyzer. A DPE audiogram is graphically presented by one of a plurality of ways, e.g. on graph paper, on a CRT screen, or in tabular form. Such DPE audiogram may graphically be presented on x-y axes with the response frequency of the DPE tone, $2f_1-f_2$, plotted as the geometric mean of such two frequencies along the x-axis of the graph. The level of each such frequency, presented in decibels, is plotted along the y-axis of the graph. The response of normal ears may be superimposed on such graph to give the hearing clinician an objective view of the DPE amplitude versus frequency response of the patient being tested as compared to a person of normal hearing. The apparatus and method for DPE audiogram testing is advantageous over traditional hearing tests in that the procedure is completely objective, that is, it does not require a patient to respond as to whether or not a test tone has been "heard" by such patient.

According to another aspect of the invention a programmed digital computer controls the generation of the input tone at particular input frequencies $f_1$, $f_2$. The input tones, having equal amplitudes, are varied in amplitude over a predetermined range, e.g., 25 to 85 db SPL. For each input amplitude, the DPE response amplitude at frequency $2f_1-f_2$ is recorded after measurement by the frequency analyzer described above. An input/output response for the particular DPE frequency response, usually represented as the geometric mean of $f_1$ and $f_2$, is graphically plotted, either on graph paper or on a CRT screen, or is displayed in tabular form. The input amplitude in db SPL in plotted along the x-axis; the DPE amplitude is plotted along the y-axis. The "noise floor" as measured by the frequency analyzer may also be presented on the graphical display, along with a "band" of output responses which have been determined to be "normal" as a function of input amplitude. The advantage of this DPE procedure over other kinds of stimulated emission testing, is that DPEs have a reasonably wide dynamic range, in terms of growth of response amplitude as a function of stimulus level, thereby permitting evaluation of cochlear function at both "threshold" and suprathreshold levels of stimulation.

According to another feature of the invention, methods and apparatuses are provided for reducing the level of background noise sensed in DPE detection. A first method and apparatus, called phase-locked DPE extraction, initiates averaging of the DPE signal from the ear canal only when such DPE signal is at a particular phase. This method assures that all of the DPE signal is added to the averaged waveform, but background noise is significantly reduced.

According to another feature of the invention, a method and apparatus for reducing the level of background sensed in DPE detection includes providing two microphones in the eartip by which tones in the ear canal are sensed. The output of the first microphone includes signals representative of the DPE tone as well as patient-induced noise, such as coughing. The output of the second microphone is adjusted such that signals of the DPE tone are not present, yet signals representative of patient induced noise are produced. When applied to the plus and minus inputs of a differential amplifier, the output of such amplifier includes the DPE signal, with a "body" or noise signal significantly reduced due to the subtraction of the two signals.

BRIEF DESCRIPTION OF THE DRAWINGS

The objects, advantages and features of the invention will become more apparent by reference to the drawings which are appended hereto and wherein like numerals indicate like parts and wherein an illustrative embodiment of the invention is shown, of which:

FIG. 7A is a traditional audiogram for a hearing impared person, while

DESCRIPTION OF THE INVENTION

This invention relates to apparatus and methods for measuring Distortion Product Emission (DPE) tones which are generated in the ear in what is believed to be a non-linear bio-mechanical feedback mechanism of the cochlea of an ear. By inducing such DPE tones, analyzing the level of such tones with respect to input tones, minimizing the noise associated with such tones, and presenting recorded tones in audiogram and input/output displays, hearing of a human being can be objectively assessed.

In order to introduce the basis for the apparatus and method of the invention, FIGS. 1, 2, 3A, 3B and 4 illustrate the physiology of the hearing process of a human being.

Figure 1:
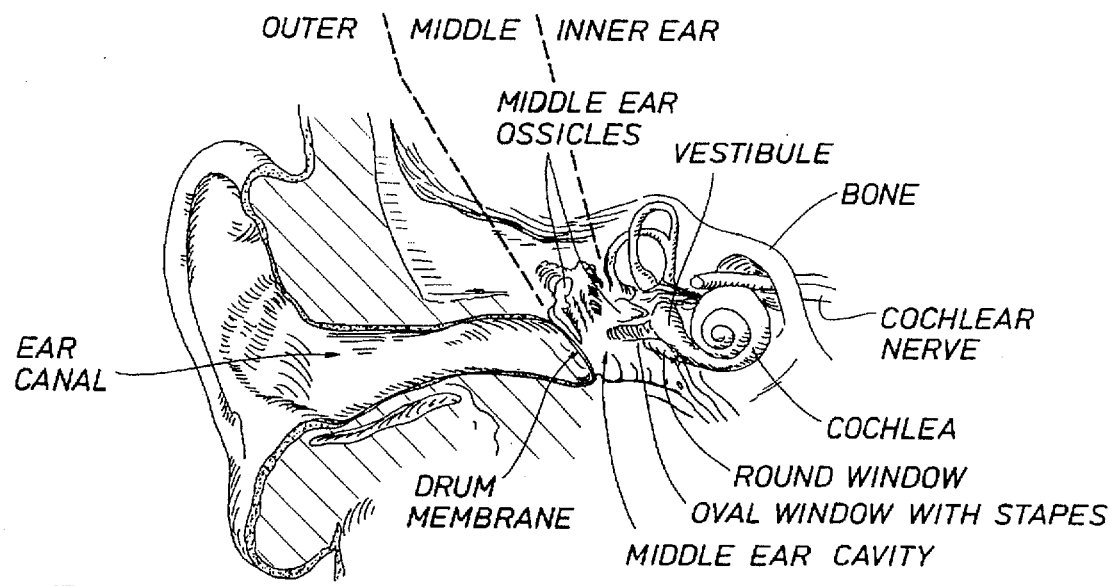
FIG. 1 is a prior art illustration of a cross-section through a human ear showing outer, middle and inner ear parts with the cochlea of the inner ear responding to tones transmitted to the middle ear, generating nerve signals via the cochlear nerve.

FIG. 1 shows a partial cross-section through a human ear with the outer, middle and inner sections of the ear illustrated. The ear canal is a passage in the outer ear which terminates with an ear drum membrane. Sound in the form of air pressure vibrations of multiple frequencies and amplitudes cause the ear drum membrane to vibrate.

Figure 3A:
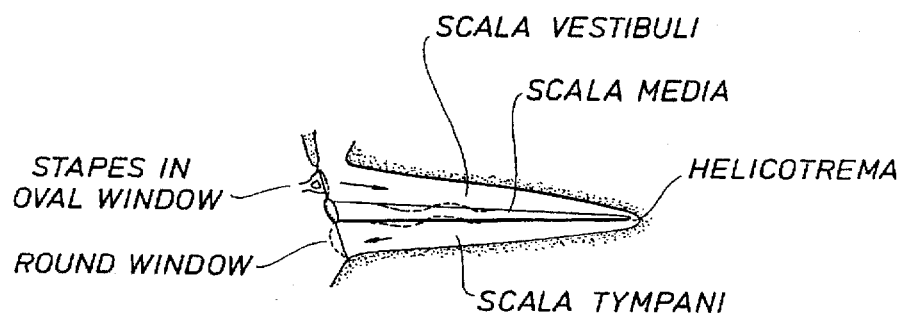
FIG. 3A is a schematic diagram of the cochlea depicted as unrolled, with a tone entering the oval window and stapes and traveling via the scala vestibuli and back via the scala tympani, while vibrating the scala media with its Basilar membrane and the Organ of Corti.

Disposed in the middle ear cavity, are ossicles, small boney structures which oscillate in response to the oscillations of the drum membrane. As shown in FIG. 3A the stapes ossicle terminates at the oval window of the cochlea of the inner portion of the ear.

Figure 2:
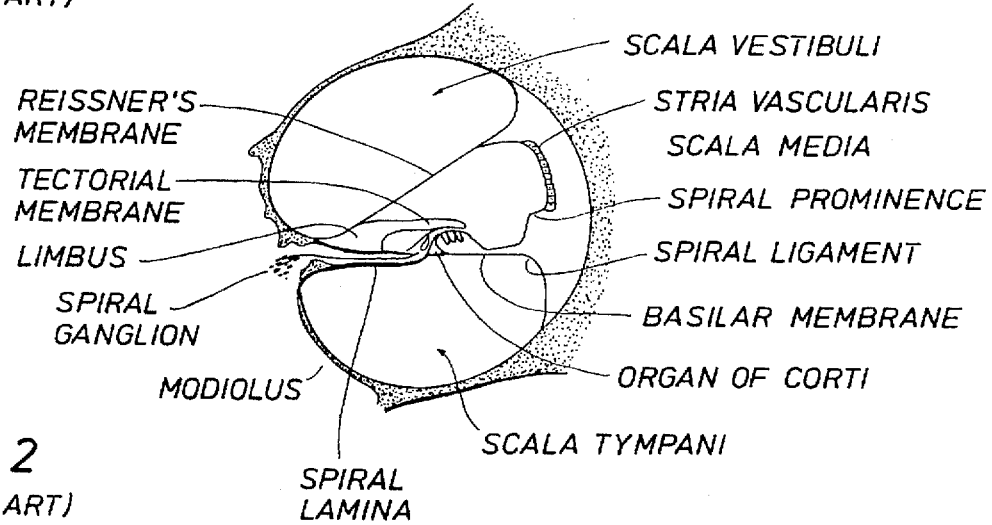
FIG. 2 is a prior art illustration of a cross-section through one portion of the cochlea, showing the placement of the Organ of Corti along the spiral of the cochlea.
Figure 4:
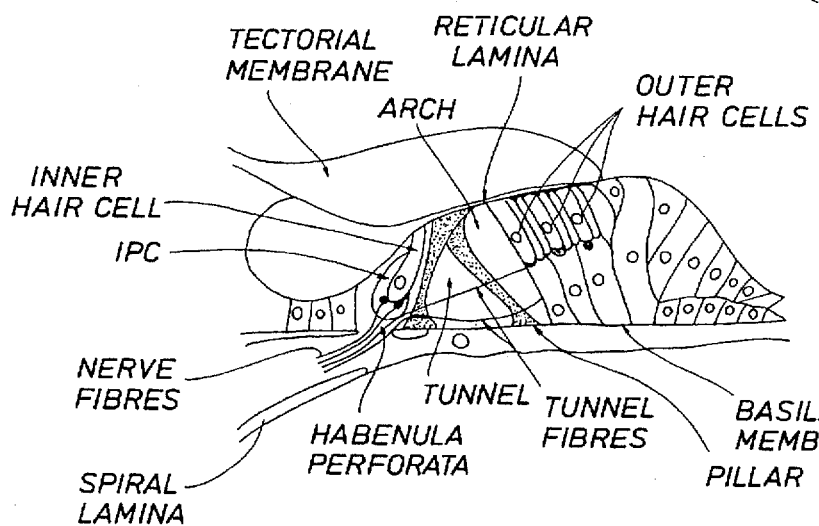
FIG. 4 is a more detailed illustration of a cross-section of the. Organ of Corti of the cochlea, in which may be seen the outer hair cells and the inner hair cells with nerve fibers connected thereto.

The cochlea (see FIGS. 1, 2, 3A, 4) is a spiral or snail like structure of the inner ear. It is a bio-mechanical organ for transforming oscillations of the stapes and the fluid of the cochlea into nerve impulses for recognition by the brain. FIG. 2 shows a cross-section through a portion of the cochlea. FIG. 3A shows a schematic diagram of an "unrolled" cochlea illustrating a sound wave entering the oval window and causing the scala media to oscillate as the sound pressure traverses the scala vestibuli and the scala tympani. As illustrated in FIG. 2, the Organ of Corti is disposed on the basilar membrane of the scala media. Accordingly, vibrations or oscillations of the scala media in response to air pressure vibrations via the outer ear canal and the vibration of the ear drum membrane, cause the Organ of Corti to vibrate. As illustrated in FIG. 4, the Organ of Corti has inner and outer hair cells disposed along the entire spiral length of the cochlea. Each inner hair cell includes nerve fibers which lead to the brain.

Figure 3B:
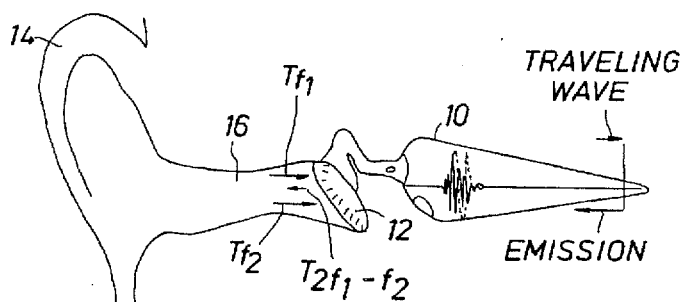
FIG. 3B is a schematic diagram illustrating tones $T_{f1}$ and $T_{f2}$ being applied to the ear drum membrane, where they enter the organ of Corti as a traveling wave, which produces a Distortion Product Emission tone of frequency $2f_1-f_2$ which is transmitted by the middle ear ossicles to the ear drum membrane, which vibrates like a speaker diaphram to transduce the DPE into acoustic energy in the ear canal.
Figure 3C:
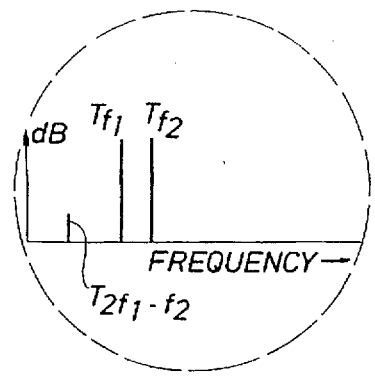
FIG. 3C is an illustration showing the relative frequencies and amplitudes of the stimulating tones and the DPE tone which is generated by the cochlea.

FIG. 3B illustrates the Distortion Product Emission phenomenon. When two audio tones are applied to the outer ear canal, such tones are simultaneously applied to the cochlea as traveling waves. Such tones, one of lower frequency $f_1$, the other of higher frequency $f_2$, are preferably applied with equal amplitude, or $f_1$ 10–15 dB larger than $f_2$, and of a frequency ratio $f_2/f_1$ of about 1.21. Under such conditions a healthy human cochlea 10 generates a lower frequency, lower amplitude tone which is sensed by the ear drum 12. FIG. 3B schematically illustrates that such tone in a human being is at a frequency of $2f_1-f_2$.

It has been discovered, as a result of tests in both normal and hearing impared ears with a number of human beings, that DPEs can form the basis of an objective hearing test. DPE testing has several advantages over the use of Transiently Evoked Emission (TEE) testing. In particular, because of the continuous, short-latency nature of the DPE, essentially any frequency, between approximately 1 and 8 kHz, can be intentionally tested. Such frequency specificity indicates that a DPE "audiogram", objectively produced, can be a substitute for, or an adjunct to a conventional audiogram, where the patient subjectively responds to tones at different frequencies and amplitudes or levels.

Moreover, it has been discovered that compared to other stimulated-emission types of responses of the human ear, the reasonably wide dynamic range of DPEs, in terms of increase of response amplitude as a function of stimulus level, permits evaluation of cochlear function at both threshold and suprathreshold levels of stimulation. This latter feature allows the use of DPEs to evaluate remaining outer hair-cell cochlear function in the ears of patients demonstrating a hearing loss up to 45–55 dB HL. In contrast, TEEs cannot typically be measured in individuals with hearing losses greater then 20–30 dBHL.

To produce DPEs, two related pure tones (e.g., $f_2/f_1=1.21$ or 1.22) are simultaneously presented to the ear. The non-linear audio response, that is distorted primarily in frequency, is believed to be generated by active, biomechanical elements of the cochlea. In particular, these non-linear elements react to the two-tone signal so that DPEs of additional, different frequencies are created. In human ears, the predominant DPE is generated at the frequency value defined by the simple algebraic expression $2f_1-f_2$. The testing for DPEs differs from the examination of TEEs in that the emissions are extracted by spectral averaging of the ear-canal signal. The spectral analysis includes emissions not only at the distortion-product frequency, but also at the frequencies of the two stimulating or primary tones, at $f_1$ and $f_2$.

Figure 5:
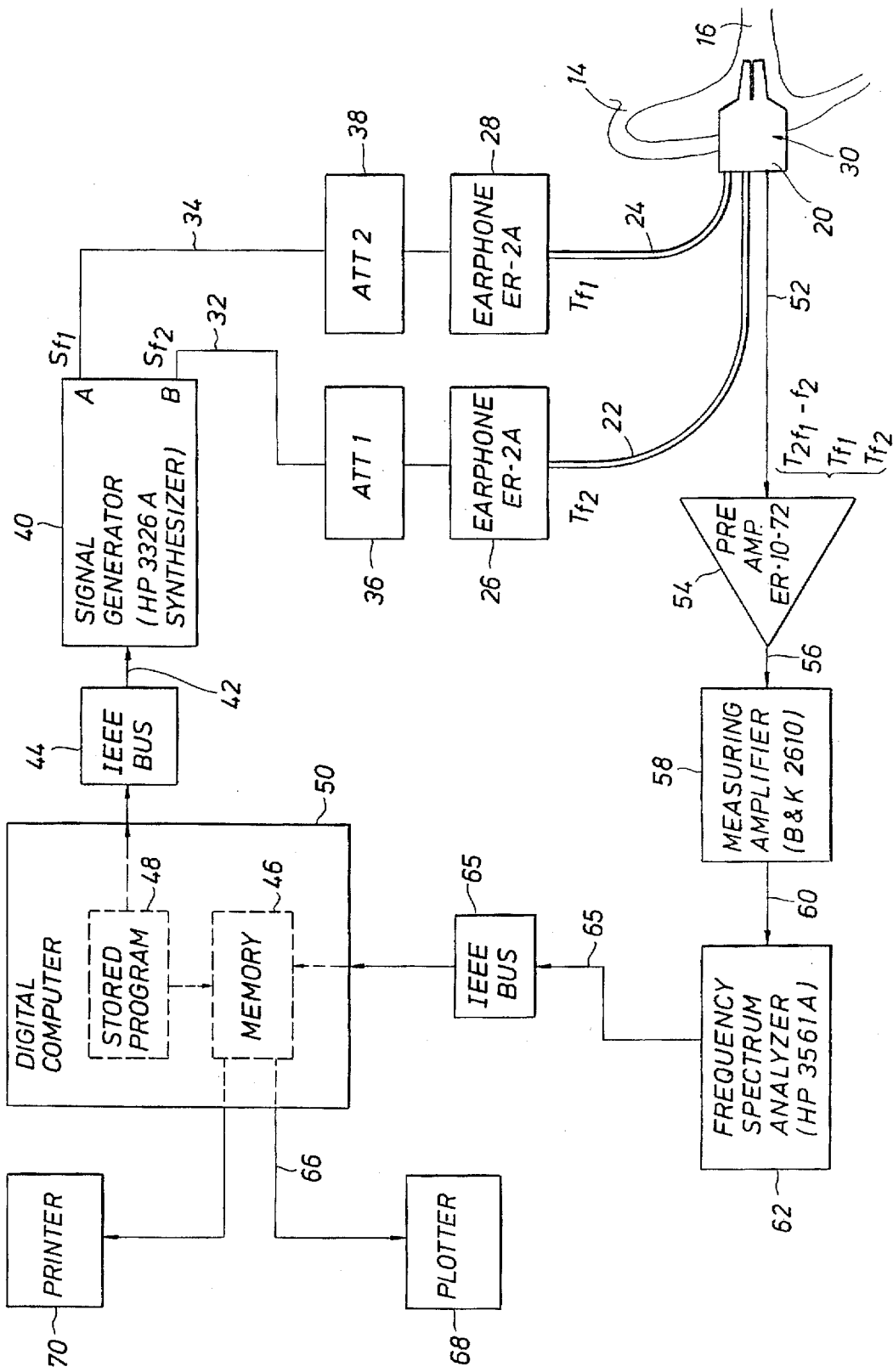
FIG. 5 is a system diagram of the apparatus necessary to produce DPE audiograms and input/output displays for assessing the hearing of a patient.

FIG. 5 illustrates, by means of a system diagram, the application of equi-level tones to the ear canal 16 of a human ear 14. A foam eartip 20 is placed in the ear canal 16. Two air ways 22, 24 are connected respectively between earphones 26 and 28 and eartip 20. The earphones or speakers 26, 28 are preferably model ER-2 speakers of Etymotic Research Corporation. Such earphones have reasonably flat responses from about 200 Hz to about 10 kHz.

The ear tip 20 also includes at least one microphone 30 which is a low-noise, miniature-microphone. Such microphone 30 is preferably model ER-10 13 of the above-mentioned Etymotic Research Corporation. It is specially designed to record low amplitude audio emissions from the human ear canal.

As illustrated in FIG. 5, a digital computer 50 preferably a Digital Equipment Computer 11/23 (but any suitable microprocessor such as an IBM PC, or equivalent may be used), is programed to step through a plurality of predetermined frequency pairs at predetermined levels or amplitudes. As mentioned above, because of the physiology of the human ear, a frequency ratio of $f_2/f_1$ is preferably about 1.21 or 1.22. The preferred levels of such frequency tones will be discussed below in conjunction with the generation of input/output plots.

Under control of the stored program 48 in computer 50, a control signal is sent to signal generator 40 via an IEEE instrumentation bus 44 and lead 42. Signal generator 40 is preferably a dual channel HP3326A synthesizer which produces, on command from computer 50, two equal level sinusoidal electrical signals on leads 32 and 34. Attenuators 36 and 38 advantageously may be placed in leads 32 and 34 between earphones 26, 28 and signal generator 50, to provide a means to precisely control the level of the primary tones, $T_{f1}$ and $T_{f2}$ applied to earphones 26 and 28 and via eartip 20 to ear canal 16. (Such attenuators preferably are Wavetek 5P programmable attenuators.)

The microphone 30 of eartip 20 is connected to pre-amplifier 54 via lead 52. Pre-amplifier 54 is preferably an Etymotic Research model ER-10-72. The DPE tone $T_{2f_1-f_2}$ as well as tones $T_{f_1}$ and $T_{f_2}$ from the ear canal 16 are amplified by preamplifier 54 and then applied to measuring amplifier 58, a Bruel and Kjaer model 2610. Next, such tones are applied to frequency spectrum analyzer 62, preferably a Hewlett Packard model 3561A, where the amplitude level of each tone signal is determined in decibels SPL. Such levels, as well as the frequencies of the input tones, $f_1$ and $f_2$, and the DPE tone $2f_1-f_2$ are applied to computer 50 memory 46 via lead 64 and IEEE instrumentation bus 65. Note: (IEEE signals are digital.)

Figure 6A:
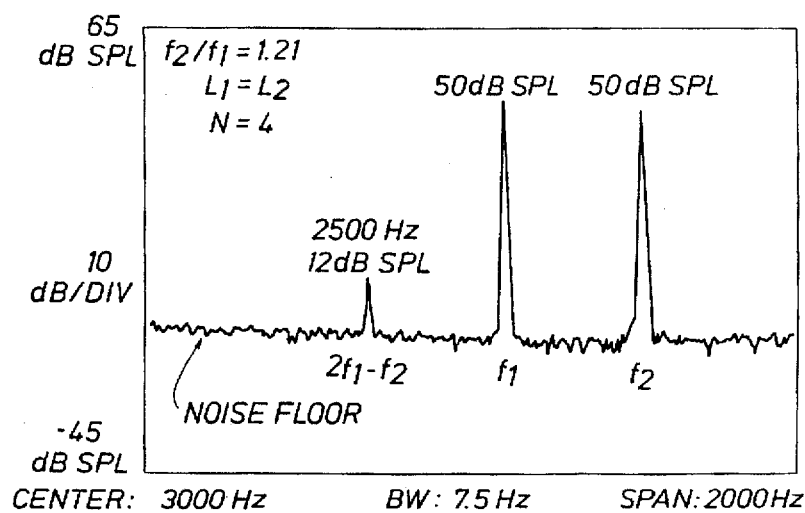
FIGS. 6A, B, C and D illustrate outputs of each DPE signal from the spectrum analyzer (6A) which are stored in computer memory (6B) and then are plotted as a DPE audiogram (6C) or as a DPE input/output display (6D).
Figure 6B:
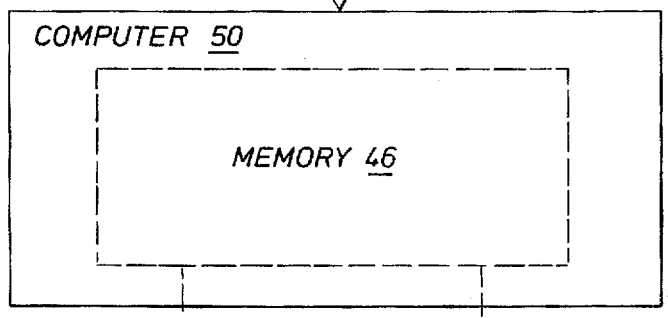

FIGS. 6A and 6B schematically illustrate the storage of the tone levels of tones $T_{2f_1-f_2}$, $T_{f_1}$ and $T_{f_2}$. The level of the noise floor is also stored.

It has been determined that the primary cochlear frequency position that contributes to the generation of the DPE at $2f_1-f_2$ is the frequency region near the geometric mean of frequencies $f_1$ and $f_2$. The geometric mean of two frequencies $f_1$ and $f_2$ is $(f_1 \times f_2)^{1/2}$. Accordingly, the levels of DPE frequencies $2f_1-f_2$ are stored in memory and plotted as described below as a function of the geometric mean frequency, $f_{geo}=(f_1 \times f_2)^{1/2}$.

According to this invention, DPE activity of a human being is specified in terms of two response measures. In the first form, illustrated at FIG. 6C, the frequency extent of cochlear function is expressed in terms of DPE amplitude as a function of stimulation frequency. Such a graphical display is called a DPE "audiogram". To obtain an objective DPE audiogram, DPEs are recorded, using the apparatus of FIG. 5, in 100 Hz steps, at three primary tone levels of 65, 75, and 85 dB SPL. The frequency ratio of the $f_1$ and $f_2$ tones are adjusted to be about 1.22 or 1.21, i.e., $f_2/f_1=1.21$ or 1.22.

Figure 6C:
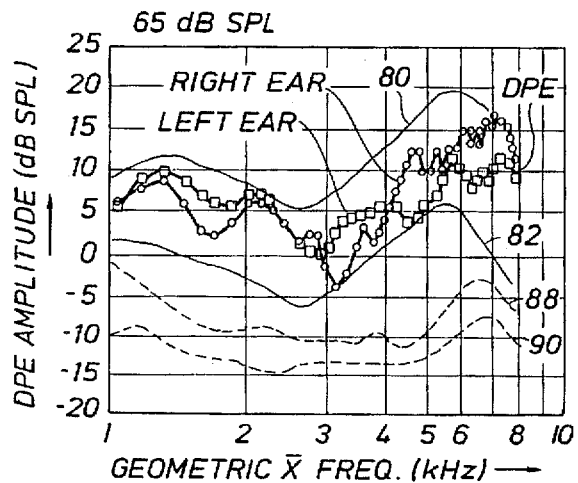
Figure 6D:
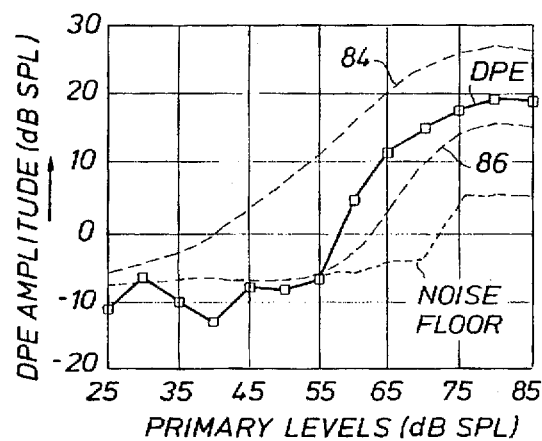

The second measure of DPE activity is shown at FIG. 6D which indicates the response/growth or input/output (I/O) aspects of DPE activity. To determine the dynamic range of the distortion-generation process, the I/O functions are determined over a 60 dB range of stimulus levels, (i.e., from 25 to 85 dB SPL). Such functions are preferably acquired at 11 discrete test frequencies, distributed in regular, ¼ octave intervals, from 1–8 kHz. The display of FIG. 6D is for one particular test frequency and shows the level response of the DPE tone as a function of increasing input tone amplitude. From the various I/O curves at the various test frequencies, information concerning the function of an ear under test can be determined. Specifically, an ear's outer hair cells at either threshold or suprathreshold sound levels can be determined.

One of ordinary skill in the digital programing art can rapidly prepare a stored program 48 and data arrangement for memory 46 to automatically collect the data for an audiogram like that of FIG. 6C and Input/Output response like that of FIG. 6D. The source code program used in a laboratory setting during the creation of this invention is attached hereto as appendix A. Such program is written in Fortran language. As indicated above, such program controls a DEC mini-computer, but the ultimate commercial version of the system of FIG. 5 will likely include a dedicated microcomputer with a stored program similar to that of Appendix A for collecting data for DPE audiograms and I/O functions.

Returning now to a more detailed explanation of the DPE audiogram of FIG. 6C, the amplitude vs. frequency bands 80, 82 represent the ± one standard deviation of a database of human DPE response as a function of DPE frequency (geometric mean of $f_1$ and $f_2$). Such bands were determined from "audiograms" of 44 ears displaying normal aural-acoustic immittance and hearing sensitivity. In FIG. 6D, bands 84 and 86 represent I/O ± one standard deviation bands at a particular frequency of such database. The noise floor of FIG. 6D represents the noise floor illustrated in FIG. 6A as recorded for the various input levels of tones $T_{f_1}$ and $T_{f_2}$. The bands 88, 90 of FIG. 6C represent ± one standard deviation of the noise floor.

Figure 7A:
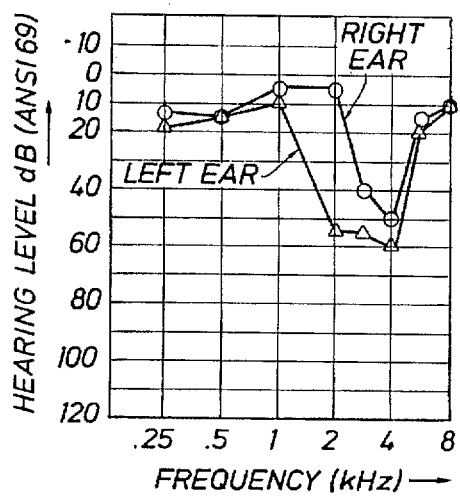
Figure 7B:
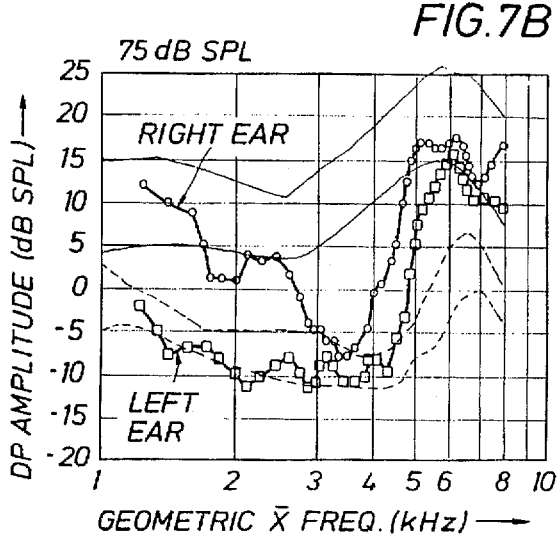
FIG. 7B is a DPE audiogram according to the invention of such person.
Figure 7C:
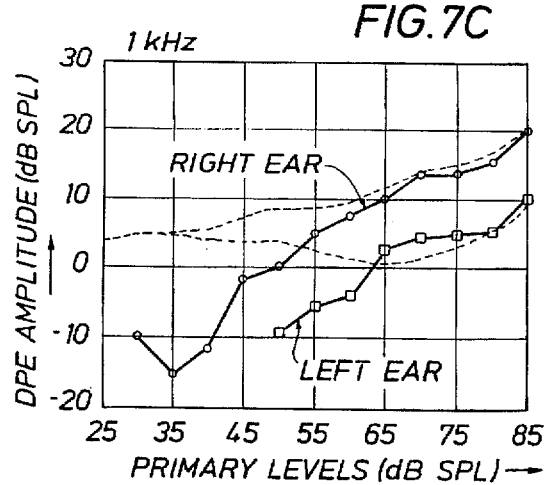
FIGS. 7C–7F are DPE input/output functions for such person.
Figure 7D:
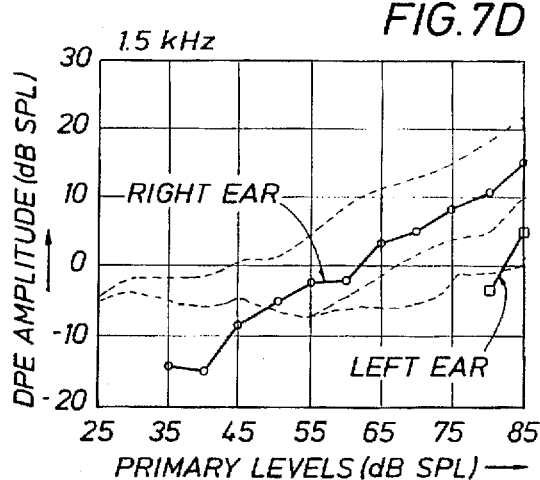
Figure 7E:
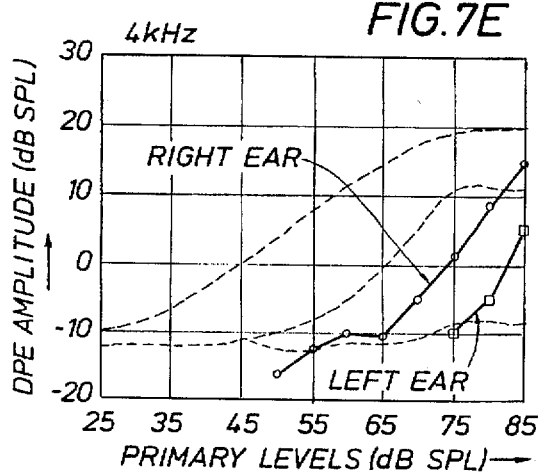
Figure 7F:
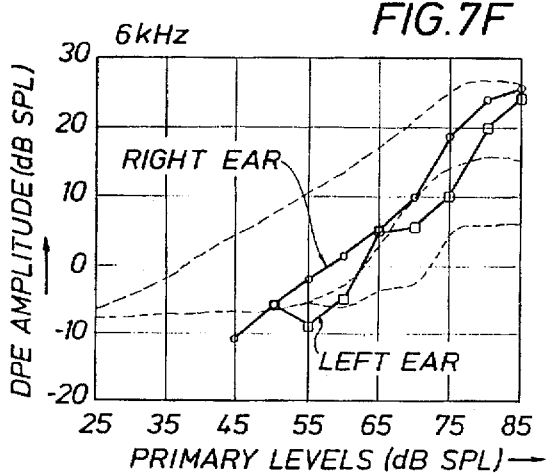

One advantage of DPE testing is that DPE emissions have the capability of accurately delimiting the boundary between normal and abnormal function. This property is illustrated best in patients exhibiting the effects of noise damage in which discrete notches and sharp reductions in high-frequency hearing commonly occur. FIGS. 7A through 7F are test results of a patient with noise-induced hearing loss due to the excessive use of recreational firearms. The standard audiograms, for each ear, are shown at FIG. 7A. At FIG. 7B, the corresponding DPE "audiograms," in response to 75-dB SPL primaries, are shown. A comparison of the DPE audiogram of FIG. 7B with that of a standard audiogram of FIG. 7A indicates that the frequency pattern of the reduction in DPE amplitudes follows very closely the details of the hearing loss depicted by standard audiometrics. That is, the function for the more damaged left ear (triangular and square symbols) declined to the level of the noise floor at a frequency that was lower than that at which the curve for the better-hearing right ear (circular symbols) descended to these levels. In addition, the finer-frequency steps of the DPE "audiogram" demonstrate that the emissions for the right ear also returned to the average range of amplitudes, at a frequency that was lower in value than that at which the responses recorded from the poorer-hearing left ear reached normal emission levels.

FIGS. 7C through 7F represent several I/O functions selected to show the outcome of the discrete-frequency, I/O testing, between 1 and 6 kHz. For example, as expected from the behavioral threshold estimated for 1.5 kHz (i.e., by interpolating between 1 and 2 kHz on the behavioral audiogram), DPE magnitudes for the right ear are within normal limits. In contrast, the left ear exhibited an estimated hearing loss between 10 and 55 dB SPL. At 1.5 kHz, DPEs were essentially nonexistent. Thus, the observed asymmetry in the frequency extent of DPE I/O activity supported the asymmetry noted in the hearing for the two ears, around 1–2 kHz. By 6 kHz, (FIG. 7F) the behavioral measures (FIG. 7A) indicate that the right ear has slightly better hearing than the left. Similarly, the DPE I/O curves for 6 kHz (FIG. 7F) support the behavioral observation in that the detection "thresholds" for the left ear are about 5 dB poorer than the comparable measures for the right ear. In general, DPEs track hearing loss due to noise exposure accurately. This is believed to be so because excessive sound injures the outer hair cells preferentially, especially in the beginning stages. It is believed that DPEs selectively test outer hair-cell functioning.

Returning to FIG. 5, both DPE audiograms and I/O functions may be graphically displayed by means of a plotter 68 under control of digital computer 50. The plotter used in the laboratory embodiment of the invention was an HP 7470A plotter, but of course, a wide variety of commercial plotters could be used as would be known to one of ordinary skill in the data processing art. Likewise printer 70, under control of computer 50 serves to provide a print-out of DPE audiograms or I/O functions. Such DPE audiograms or I/O functions may also advantageously be displayed on a CRT or the like (not illustrated).

Figure 8A:
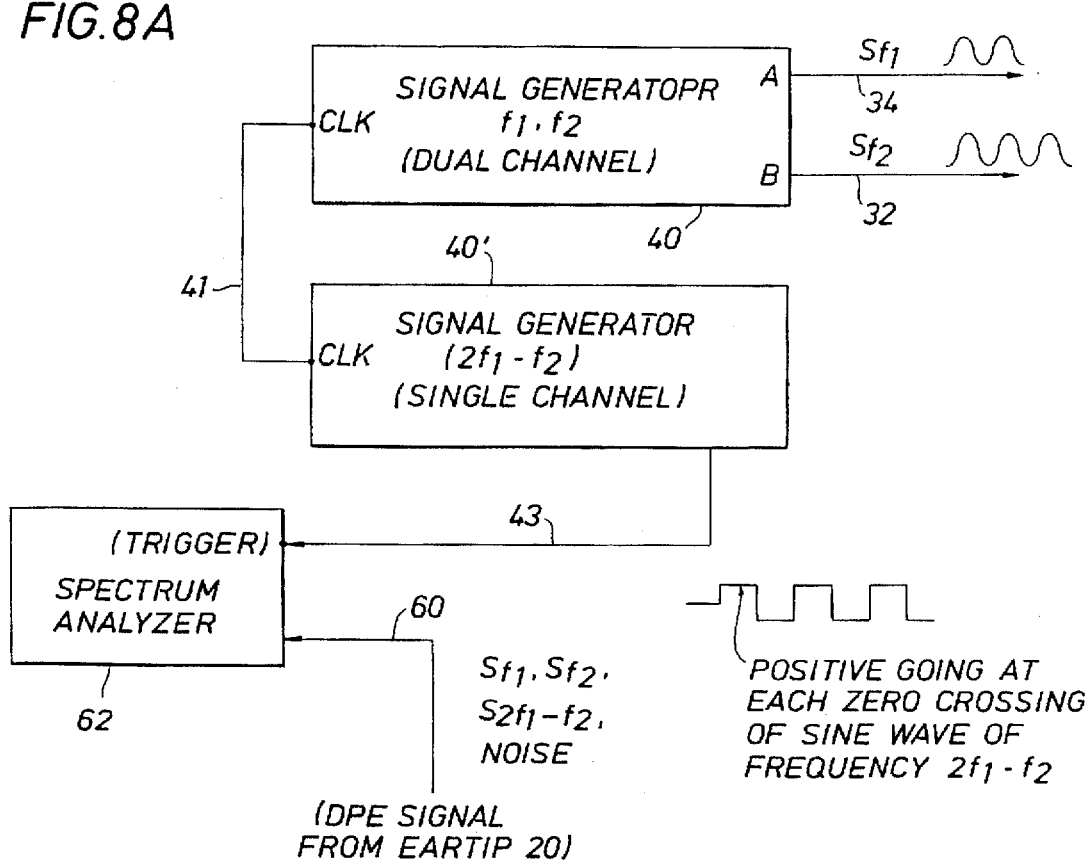
FIGS. 8A and 8B illustrate two embodiments of the phase-locked averaging feature of the invention by which the noise floor of the DPE signal is reduced.

Turning now to FIG. 8A, an illustration of the phase-locked averaging of the DPE signals is shown which is performed in order to reduce the noise level or "floor" shown at FIG. 6A. A signal generator 40 as shown in FIG. 5 is provided to generate signals $S_{f1}$ and $S_{f2}$ on leads 32, 34. The master clock of signal generator 40 (Hewlett Packard 3326A) is connected to the master clock of single channel signal generator 40'. Signal generator 40' is set to the DPE frequency $2f_1-f_2$. Connection of the master clocks of signal generators 40 and 40' insures that there is no phase drift among any of the three signals, i.e., $S_{f1}$, $S_{f2}$, $S_{2f1-f2}$, because all clocks are synchronized.

Signal generator 40' produces a square wave output on lead 43 such that its positive going pulse is synchronized with the positive going sine wave of frequency $2f_1-f_2$. Such square wave of frequency $2f_1-f_2$ is applied to the trigger input of spectrum analyzer 62. A time average is determined by real-time spectrum analyzer 62 each time it is triggered by the positive going zero crossing signal on lead 43. Accordingly, the time average of the DPE signal is initiated for each sample of the DPE signal at the same phase of such DPE signal. Such procedure assures that all of the DPE signal is added to the averaged waveform, but noise signals of different frequencies than that of the DPE signal will be out of phase from sample to sample. Accordingly, the noise signal, dissimilar in phase, is substantially reduced during the averaging process.

Once the time averaged waveform has been collected, spectrum analyzer 62 uses standard Fourier-transform techniques to determine the level of the DPE signal, and of course the noise floor for frequencies other than that of the DPE signal. Using the method and apparatus of FIG. 8A to augment that of FIG. 5, background noise is reduced by approximately 15 dB below that observed without the phase-locking method and apparatus.

Figure 8B:
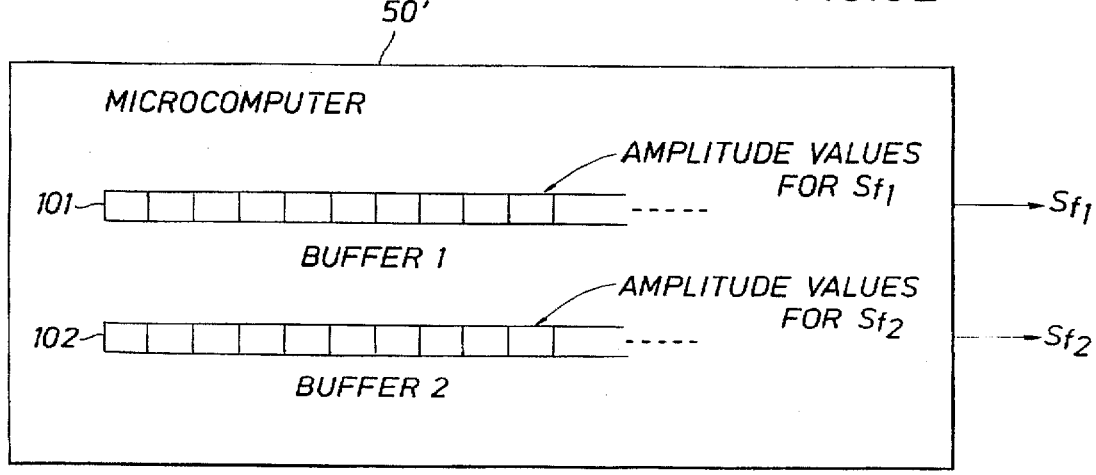

The phase-locking feature of the invention described above provides a means for repeatedly initiating a time sample at the same phase of the DPE signal. An alternative method for accomplishing such phase-locking is illustrated in FIG. 8B. Rather than using a stand-alone signal generator 40, signals $S_{f1}$ and $S_{f2}$ are generated by microcomputer 50. Two wave form buffers are established in the memory of computer 50'. The buffers 101, 102 store the digitized time values for $S_{f1}$ and $S_{f2}$.

Each buffer is set to an integer multiple of the length of the DPE period. After output of each point in the buffer, exactly one period of an integer multiple of the period of the DPE signal has elapsed. For example, if a buffer contains 1,000 points for an output signal, representing 1 microsecond per point, such buffer is equivalent to a DPE frequency of 1 kHz each time the information in the buffer is completed.

Another alternative approach, one not involving computer generation of the primary-tone signals, provides a computer clock running at the period of the DPE frequency. For example, if the clock is set to "tick" once per microsecond, 1,000 ticks would be equivalent to 1 millisecond, i.e., the period of a 1-kHz DPE. At the end of every 1,000 ticks, an interrupt would be generated to instruct the computer to initiate another time sample. If the time sample is longer than one period of the distortion-product frequency, the computer would simply wait until the next 1,000 ticks have elapsed. With the clock running continuously, the phase of the distortion product would be constant from sample to sample.

Figure 9A:
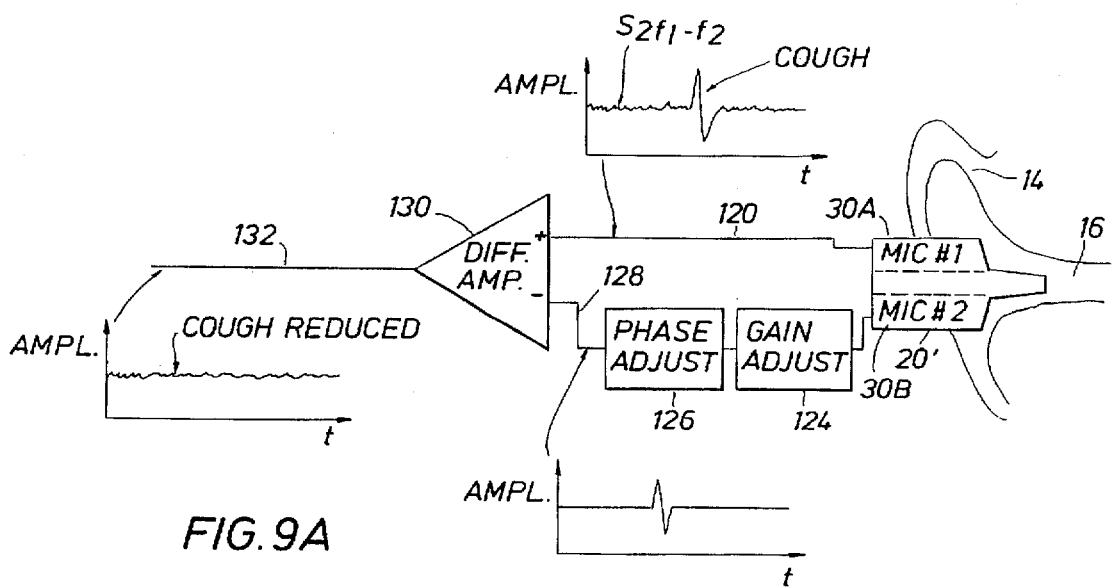
FIG. 9A schematically illustrates a two-microphone embodiment of the apparatus by which body noises such as coughs and the like may be minimized during the measurement of the DPE signal.

FIG. 9A illustrates still another apparatus and method for reducing noise when measuring DPE signals. A significant amount of body noise is created by the patient during the measurement. Coughing, sneezing and other body noises contaminate the DPE signal. FIG. 9 shows that two microphones 30A, 30B are placed in ear canal 16 to pick up the DPE signal. The output of one microphone 30A is applied via lead 120 to the plus input of differential amplifier 130. The output of a second less sensitive microphone 30B is applied via lead 122 through variable gain amplifier and phase shifter circuits 124, 126 via lead 128 to the minus input of differential amplifier 130. The output of microphone 30B is of less sensitivity so that the frequency component of $S_{2f1-f2}$ (the DPE signal) is missing from the signal applied to the minus input of differential amplifier. The gain and phase of this signal via lead 128 are then adjusted to yield maximum cancellation when applied to differential amplifier 130. That part of the lower frequency signal appearing on lead 128 due to the bodily noise is relatively unchanged. As a result, the output of differential amplifier 130 produces on lead 132 a signal comprising the DPE signal, with the body noise signal greatly reduced.

Various modifications and alterations in the described methods and apparatus will be apparent to those skilled in the art of the foregoing description which does not depart from the spirit of the invention. For this reason, these changes are desired to be included in the appended claims. The appended claims recite the only limitation to the present invention. The descriptive manner which is employed for setting forth the embodiments is to be interpreted as illustrative but not limitative.

APPENDIX A

```
C
C       MAIN PROGRAM DPOAE
C
C       BYTES
C
        BYTE  PTB(20),RIT(20),DSPF(10)
        BYTE  IDATE(9),SETNAM(6),OLDSET(6),CTLFIL(11),RTYPE
        BYTE  XFRFIL(16),GRFILE(11),CORFIL(11),SJT,AFT,NFR,PRSW,GRD
C
C       DIMENSIONS
C
        DIMENSION  CFRO(4),DBO(4),DPO(4),RNO(4)
C
C       COMMONS
C
        COMMON /COM001/ CORFIL,GRFILE,XFRFIL,RTYPE,NFR,PRSW,GRD,SJT,AFT
        COMMON /COM002/ ILOG,LR,IYA,XLO,YLO,XHI,YHI,AX,XLN,XSCALE,YLN,YSCALE
        COMMON /COM003/ DPKHZ,FAKHZ,FAATTN,FBKHZ,FBATTN,DBSPL,STZ,STP,TDB
        COMMON /COM004/ CFRO,DBO,DPO,RNO
        COMMON /COM005/ XINC,XLBINC,YINC,YLBINC
        COMMON /COM006/ RNOISE,DPAMP
        COMMON /COM009/ IPTB,IRIT,PTB,RIT
        COMMON /COM010/ SETNAM,OLDSET
C
C       DATA
C
        DATA LR    /55/       !GRAPH EDGE REF., 55 X AND 55 Y
        DATA NBRAVG /4/
        DATA CRIT  /5.0/
        DATA VN    /1.07/
        DATA SPAN  /10.0/
C
        DATA SETNAM /6*' '/
        DATA OLDSET /6*' '/
        DATA CORFIL,GRFILE /11*' ',11*' '/
        DATA XFRFIL /'D','1','G',':',12*' '/
        DATA RTYPE,PRSW,NFR,GRD,SJT,AFT /'I','Y','Y','Y','R','N'/
C
C       ............................................................
C
C       PROGRAM STARTS
C
5       CALL SCFUNC(1,N,N)
        CALL SCFUNC(3,1,1)
        WRITE (5,10) VN
10      FORMAT(1X,'              DISTORTION PRODUCT'/1X,
       +'          OTOACOUSTIC EMISSION COLLECTION PROGRAM'/1X,
       +'                 VN. ',F5.2)
C
        CALL DATE(IDATE)
        IF (IDATE(1) .EQ. ' ') STOP 'ENTER DATE THEN RE-RUN PROGRAM'
C
        J = IBUP(2,0)        !CLEAR ALL DEVICES
```

1

```
        J = IBUP(10)          !FINISH
C
C Set synthesizer to safe levels and tones
C
        CALL HPCHAN ('B')
        CALL HPATTN (80.0)
        CALL HPFREQ (30.0)
        CALL HPCHAN ('A')
        CALL HPATTN (80.0)
        CALL HPFREQ (30.0)
C
380     CALL SCFUNC(3,6,1)
        WRITE (5,400) 27
400     FORMAT(1X,1A1,'[0J','ENTER CONTROL FILE: ',$)
C
        READ (5,600) CTLFIL
600     FORMAT(11A1)
C
        CALL FILXST(IX,CTLFIL)
        IF (IX .GT. 0) GO TO 800
C
        CALL TEKOUT(7)
        GO TO 380
C
C       READ CONTROL FILE DATA
C
800     CALL ASSIGN(2,CTLFIL)
        CALL RDCNFL(1,IERR,NBRAVG,SPAN,CRIT)
C
        IGP = 1
        CALL FILXST(IX,GRFILE)
        IF (IX .GT. 0) GO TO 900
        IGP = 0
        CALL INSERT('NONE       ',GRFILE,1,11)
C
900     ICOR = 1
        CALL FILXST(IX,CORFIL)
        IF (IX .GT. 0) GO TO 1000
        ICOR = 0
        CALL INSERT('NONE       ',CORFIL,1,11)
C
1000    CALL DPPPRM(NTYPE,CRIT,NBRAVG,SPAN,STP,IGP,ICOR)
C
        NTYPE = 0                !DEFAULT TO I/O
        IF (RTYPE .EQ. 'A') NTYPE = 1    !ELSE, AUDIOGRAM
        IF (RTYPE .EQ. 'R') NTYPE = 2    !OR RATIO
C
        CALL MACTIT(XFRFIL,DSPF,RTYPE,SJT)
C
        WRITE (5,1100) 27,7
1100    FORMAT(1X,1A1,'[97a^I6C^I6Q\',1A1)
```

2

```
C
        IF (NTYPE) GO TO 1150
        CALL DPIOEX(NTYPE,ICOR,IGP,NBRAVG,SPAN,CRIT,CTLFIL,DSPF)
        GO TO 1200
C
1150    CALL DPAREX(NTYPE,ICOR,IGP,NBRAVG,SPAN,CRIT,DSPF)
C
1200    IF (AFT .NE. 'Y') GO TO 5
C
        WRITE(5,1210)27,XFRFIL
1210    FORMAT(1X,1A1,'[97a\.^C',
      +  'R KERM11^M\>SEND ',16A1)
C
        WRITE (5,1220) 7
1220    FORMAT(1X,'^M^#1N\>^C\.R DPOAE^M\',1A1)
C
        END
XXXXXXXXXXXXXXXXXXXXXXXXXXXXXXXXXXXXXXXXXXXXXXXXXXXXXX

BEGINNING OF SUBROUTINES IN ALPHABETICAL ORDER

SUBROUTINE  CFRKHZ(ICOR,XFRFIL,CTLFIL,CORFIL,WRBF)
C
        BYTE  CFRFIL(16),CTLFIL(11),CORFIL(11),WRBF(150),TSTB(6)
C
C
C.............................................................
C       SUBR STARTS
C
        IP = 1
C
        DO 100 I = 1,150
        WRBF(I) = ' '
100     CONTINUE
C
        IF (.NOT. (ICOR)) GO TO 1000
        CALL ASSIGN(3,CORFIL)
C
200     READ (3,300) CFR,X
300     FORMAT(2F9.3)
C
        IF (CFR .EQ. 999.0) GO TO 500
        IF (IP .GT. 1) WRBF(IP-1) = 9
        ENCODE (6,400,WRBF(IP)) CFR
400     FORMAT(F6.3)
C
        IP = IP + 7
        GO TO 200
C
500     IP = IP - 2
```

```
            REWIND 3
C
            GO TO 2000
C
1000  REWIND 2
C
            DO 1200 I = 1,5
            READ (2,1100) TSTB
1100  FORMAT(6A1)
1200  CONTINUE
C
1300  READ (2,1400,ERR=1500) TSTB,CFR
1400  FORMAT (2X,6A1,2X,F7.3)
C
            IF (TSTB(1) .EQ. 'S') GO TO 1300
            IF (TSTB(1) .EQ. '_') GO TO 1500
C
            IF (IP .GT. 1) WRBF(IP-1) = 9
            ENCODE (6,400,WRBF(IP)) CFR
C
            IP = IP + 7
            GO TO 1300
C
1500  IP = IP - 2
            REWIND 2
C
            DO 1600 I = 1,5
            READ (2,1100) TSTB
1600  CONTINUE
C
2000  WRITE (1,2100) (WRBF(J),J=1,IP)
2100  FORMAT(150A1)
C
            RETURN
            END

SUBROUTINE  DPAREX(NTYPE,ICOR,IGP,NBRAVG,SPAN,CRIT,PFIL)
C
C     BYTES
C
            BYTE  PTB(20),RIT(20)
            BYTE  PFIL(10),WRBF(150),EB
            BYTE  IDATE(9),SETNAM(6),OLDSET(6),RTYPE
            BYTE  XFRFIL(16),GRFILE(11),CORFIL(11),SJT,AFT,NFR,PRSW,GRD
C
C     DIMENSIONS
C
            DIMENSION  CFRO(4),DBO(4),DPO(4),RNO(4),TNS(50)
C
C     COMMONS
C
```

```
      COMMON /COM001/ CORFIL,GRFILE,XFRFIL,RTYPE,NFR,PRSW,GRD,SJT,AFT
      COMMON /COM002/ ILOG,LR,IYA,XLO,YLO,XHI,YHI,AX,XLN,XSCALE,YLN,YSCALE
      COMMON /COM003/ DPKHZ,FAKHZ,FAATTN,FBKHZ,FBATTN,DBSPL,STZ,STP,TDB
      COMMON /COM004/ CFRO,DBO,DPO,RNO
      COMMON /COM006/ RNOISE,DPAMP
      COMMON /COM009/ IPTB,IRIT,PTB,RIT
      COMMON /COM010/ SETNAM,OLDSET
C
C
C
C.........................................................................
C
C     SUBR. STARTS
C
C     PLOT X/Y AXIS, TICS, & LABELS
C
      IF (.NOT. (IGP)) GO TO 5
      CALL DPARP(NTYPE)
      CALL TCPPLT(1,450,460)       !PUT FILE NAME ON GRAPH
      WRITE (5,3300)  31,PFIL
      CALL TCPPLT(1,450,445)
      WRITE (5,3310)  31,(PTB(J),J=1,IPTB)
      CALL TCPPLT(1,450,430)
      WRITE (5,3310)  31,(RIT(J),J=1,IRIT)
C
5     EB = 'E'
      IEOF = 0
      CALL SCCA(ICC)
      CALL IPOKE("44, IPEEK("44) .OR. "050100)
C
10    KEY = ITTINR()          !FLUSH ANY PREV. KEYS
      IF (KEY .GE. 0) GO TO 10
C
C
      IF (PRSW .EQ. 'Y') CALL DPPRNT(1,NTYPE,CFR,DBSPL,DPAMP,RNOISE,PFIL)
      IF (.NOT. (ICOR)) GO TO 150    !SKIP IF NO CORREC. FILE
      CALL ASSIGN (3,CORFIL)         !ELSE, OPEN IT
C
150   IPASS = 0
C
200   IW = 1                 !WRITE POINTER = 1
      IF (PRSW .NE. 'Y') GO TO 220
      IF (.NOT. (IPASS)) CALL DPPRNT(2,NTYPE,CFR,DBSPL,DPAMP,RNOISE,PFIL)
C
220   CALL RDCNFL(2,IEOF,NBRAVG,SPAN,CRIT) !READ CONTROL DATA
      IF (IEOF) GO TO 2000              !OUT, IF EOF
      DBSPLM = DBSPL                    !SAVE ORIG. dB
      STEP  = STZ                       !SAVE dB STEP SIZE
C
      ILC = INT((DBSPL - TDB) / STZ) + 1 !CALC. NUMBER OF LOOPS
      IF (IPASS) GO TO 300
```

5

```
C
        IP = 1
        DX = DBSPL
        DO 250 I = 1,ILC
        ENCODE (3,230,WRBF(IP)) INT(DX)
230     FORMAT(I3)
C
        DX = DX - STZ
        IP = IP + 4
        WRBF(IP-1) = 9
250     CONTINUE
C
        IP = IP - 2
        WRITE (1,260) (WRBF(J),J=1,IP)
260     FORMAT(150A1)
C
C Set analyzer to set-up for this run.
C
300     CALL SNDSET(NBRAVG,SPAN)
C
        CDB = 0.0                        !DB CORRECTION = 0 dB
        IF (ICOR) READ (3,310) CFR,CDB   !READ CORRECTION FACTORS
310     FORMAT(2F9.3)
C
        IWF = 0
        DO 1000 I = 1,ILC    !NO. OF DP MEASUREMENTS LOOP
        KEY = ITTINR()       !READ KEYBOARD
        IF (KEY .EQ. 3) GO TO 2000  !LEAVE LOOP IF INPUT
        ISV = I              !SAVE FILE NUMBER POINTER
C
C Set synthesizer frequency, attenuation
C
        CALL NSFLRJ(TNS(ISV),CRIT,CDB,IPASS,NFR)
C
C       IF NO CORRECTION FACTORS, FREQ. = DPKHZ, CDB = 0.0.
C       FOR RATIO TYPE, FREQ = RATIO OF B / A
C
        IF (.NOT. (ICOR)) CFR = DPKHZ
        IF (NTYPE .EQ. 2) CFR = FBKHZ / FAKHZ
C
        CALL DPDSPD(IGP,NTYPE,IPASS,CFR,DPAMP,RNOISE,DBSPL,ISV,PFIL)
        IF (PRSW .EQ. 'Y') CALL DPPRNT(5,NTYPE,CFR,DBSPL,DPAMP,RNOISE,PFIL)
C
C       Write out the DPamp value, paired with DPKHZ
C
        IF (IWF) GO TO 700
        ENCODE (7,650,WRBF(IW)) CFR
650     FORMAT(F7.3)
C
        IWF = 1
        IW = IW + 8
```

```
        WRBF(IW-1) = 9
C
700     ENCODE (7,650,WRBF(IW)) DPAMP
        IW = IW + 8
        WRBF(IW-1) = 9
        ENCODE (7,650,WRBF(IW)) RNOISE
        IW = IW + 8
        WRBF(IW-1) = 9
C
C Calculate next attenuation, applying DB step size.  Ensure also that
C dBattn has not reached max and that DPamp is still above the noise level.
C
        FAattn = FAattn + STZ
        IF (FAATTN .GT. 80.0) GO TO 1100
        FBattn = FBattn + STZ
        IF (FBATTN .GT. 80.0) GO TO 1100
        dBSPL = dBSPL - STZ
C
1000    CONTINUE
C
1100    IPASS = 1          !AT LEAST 1 PASS COMPLETED
        IW = IW - 2
        WRITE (1,260) (WRBF(J),J=1,IW)
C
        GO TO 200    !NEXT GROUP IF NOT DOUBLE CTRL/C
C
2000    CALL HPCHAN ('B')       !MAX VALUES TO SYNTHESIZER
        CALL HPATTN (80.0)
        CALL HPFREQ (30.0)
        CALL HPCHAN ('A')
        CALL HPATTN (80.0)
        CALL HPFREQ (30.0)
        KSV = KEY
C
        WRITE (1,3020) EB
3020    FORMAT(1A1/)
C
        CALL CLOSE (1)
        CALL CLOSE (2)
        IF (ICOR) CALL CLOSE(3)
        IF (IGP) CALL CLOSE (4)
        CALL IPOKE("44,IPEEK("44) .AND. (.NOT. "050100))
3010    KEY = ITTINR()          !FLUSH ANY PREV. KEYS
        IF (KEY .GE. 0) GO TO 3010
        CALL SCCA
C
        IF (KSV .NE. 3) GO TO 3060
        IF (AFT .NE. 'Y') GO TO 6000
C
        WRITE (5,3050) 24
3050    FORMAT(/$1X,1A1,'FILE TRANSFER TO MAC AS SELECTED? [N/Y]: ')
```

```
C
        READ (5,3100) AFT
C
        GO TO 6000
C
3060   IF (.NOT. (IGP)) GO TO 6000  !SKIP IF NOT IN GRAPH MODE
        IF (GRD .EQ. 'N') GO TO 6000 !SKIP IF NO DUMP TO PRINTER
C
        CALL ASSIGN (1,XFRFIL)
        READ (1,3100) WRBF(1)
        READ (1,3100) WRBF(1)
        READ (1,3100) WRBF(1)
        READ (1,3100) WRBF(1)
        READ (1,3100) WRBF(1)
        READ (1,3100) WRBF(1)
3100   FORMAT(1A1)
C
C      SEND GRAPH TO PRINTER
C
        CALL DPARP(NTYPE)
        CALL DATE(IDATE)
C
        CALL TCPPLT(1,450,450)      !PUT DATE ON GRAPH
        WRITE (5,3200) 31,IDATE
3200   FORMAT(1X,1A1,9A1,$)
C
        CALL TCPPLT(1,450,430)      !PUT FILE NAME ON GRAPH
        WRITE (5,3300) 31,PFIL
3300   FORMAT(1X,1A1,10A1)
C
        CALL TCPPLT(1,450,410)
        WRITE (5,3310) 31,(PTB(J),J=1,IPTB)
3310   FORMAT(1X,1A1,20A1)
        CALL TCPPLT(1,450,390)
        WRITE (5,3310) 31,(RIT(J),J=1,IRIT)
C
        IPASS = 0
C
3500   READ (1,3600,END=5100) N,WRBF
3600   FORMAT(Q,150A1)
C
        IF (WRBF(1) .EQ. 'E') GO TO 5100
        DECODE (7,650,WRBF(1)) CFR
        IW = 9
C
        DBSPL = DBSPLM
C
        DO 5000 I = 1,3
        ISV = I
        IYA = ((I * 150) - 150) + 40    !Y ADJUSTER
C
```

8

```
        DECODE (7,650,WRBF(IW),ERR=5000) DPAMP
        IF (DPAMP .EQ. 0.0) GO TO 5000
        IW = IW + 8
        DECODE (7,650,WRBF(IW)) RNOISE
        IW = IW + 8
C
        CALL DPARPL(1,CFR,DBSPL,DPAMP,RNOISE,IPASS,ISV)
C
        IF (IPASS) GO TO 5000
        IY = ((I * 150) - 150) + 40    !Y OFFSET FOR FILES 1 TO 3
        CALL TCPPLT(1,375,IY)
        WRITE (5,4010) 31,INT(DBSPL)
 4010   FORMAT(1X,1A1,'LEVEL ',I3,' dB SPL')
C
        DBSPL = DBSPL - STEP
C
 5000   CONTINUE
C
        IPASS = 1
        GO TO 3500
C
 5100   CALL CLOSE (1)
        CALL CLOSE (4)
C
        WRITE (5,5200) 27,23
 5200   FORMAT(1X,2A1)
C
 6000   CALL TEKOUT(24)
C
        RETURN
        END
        SUBROUTINE DPARP(NTYPE)
C
        BYTE CORFIL(11),GRFILE(11)
C
        COMMON /COM001/ CORFIL,GRFILE
        COMMON /COM002/ ILOG,LR,IYA
C
C ....................................................
...
C       SUBR. STARTS
C
        CALL GPFPRM(NTYPE,GRFILE)    !READ GRAPH PARAMS
C
        ITITLE = 1
        IFRL = 1
        DO 20 I = 1,3          !3 PLOT LOOP
C
        IYA = ((I * 150) - 150) + 40    !Y ADJUSTER
        CALL DPPLT1(NTYPE,ITITLE,IFRL)    !SET UP GRAPH
```

```
            ITITLE = 0
            IFRL = 0
    C
    20      CONTINUE
    C
    C       PLOT AVG. +/- ST.DEV DATA
    C
            WRITE (5,30) 27,97      !MAKE DOTTED LINES
    30      FORMAT(1X,2A1,$)
    C
            DO 100 I = 1,3          !3 PLOT LOOP
            IYA = ((I * 150) - 150) + 40    !Y ADJUST
    C
            DO 50 J = 1,4           !4 ST.DEV LINES
            IBP = 1         !IBP POINTS TO CHAR 29 (GS) TO INIT PLOT
            CALL DPPLT2(IBP,IPERR)  !PLOT LINES
            IF (IPERR) GO TO 110    !110 = EOF
    50      CONTINUE
    C
    100     CONTINUE        !3 PLOT LOOP TARGET
    C
    110     CALL CLOSE (3)  !CLOSE FILE
    C
            WRITE (5,30) 27,96      !RETURN TO SOLID LINES
    C
            RETURN
            END
            SUBROUTINE   DPARPL(ISKW,CFR,DBSPL,DPAMP,RNOISE,IPASS,ISV)
    C
            DIMENSION  CFRO(4),DBO(4),DPO(4),RNO(4)
    C
            COMMON /COM002/ ILOG,LR,IYA,XLO,YLO,XHI,YHI,AX,XLN,XSCALE,YLN,YSCALE
            COMMON /COM004/ CFRO,DBO,DPO,RNO
    C
    C
    *********************************************************************
    *****
    C       SUBR. STARTS
    C
            IP = ISV                !TEXT POINTER = FILE NO.
            IY = ISV                !Y POINTER = FILE NO.
            IX = 375                !MAX X = 325
            IF (IY .GT. 3) IY = 3   !DISPLAY NO MORE THAN 3 GRAPHS
            IF (IP .GT. 4) IP = 4   !NO MORE THEN 4 INFO. GROUPS
            IY = ((IY * 150) - 150) + 40    !Y OFFSET FOR FILES 1 TO 3
            IF (IP .GT. 3) IY = 415 !Y OFFSET FOR BEYOND 3RD FILE
    C
            IF (ISKW) GO TO 600     !SKIP IF PLOT DATA, NOT TEXT
    C
            WRITE (5,200) 31,27,127 !ERASE SEQ. FOR MAC
    200     FORMAT(1X,3A1,$)
```

```
C
        CALL TCPPLT(1,IX,IY)      !ERASE PREV. TEXT
        WRITE (5,300) 31,CFRO(IP),DBO(IP),DPO(IP),RNO(IP) !REWRITE = ERASE
300     FORMAT (1X,1A1,4(' ',F7.3))
C
        CALL TEKOUT(13)
C
        CALL TCPPLT(1,IX,IY)  !DISPLAY CURRENT DATA
        WRITE (5,300) 31,CFR,DBSPL,DPAMP,RNOISE
C
600     IBP = 1
        IF (IPASS) IBP = 2
C
        IYA = IY
        IF (IP .GT. 3) GO TO 1000
        IF (IPASS) CALL PLTLIN(1,1,IX,IY,1,CFRO(IP),DPO(IP))
        CALL PLTLIN(1,1,IX,IY,IBP,CFR,DPAMP)
        CALL PLTCRS(IX,IY,2)
        IF (IPASS) CALL PLTLIN(1,1,IX,IY,1,CFRO(IP),RNO(IP))
        CALL PLTLIN(1,1,IX,IY,IBP,CFR,RNOISE)
C
1000    CFRO(IP) = CFR              !UPDATE AS PREV. INFO
        DBO(IP) = DBSPL
        DPO(IP) = DPAMP
        RNO(IP) = RNOISE
C
        RETURN
        END
        SUBROUTINE  DPCDFX(IFN,FIL)
C
        BYTE FIL(16)
C
C........................................................
......
C       SUBR STARTS
C
        IP = (INDEX(FIL,'.')) + 1
        ENCODE (3,3150,FIL(IP)) IFN    !ENCODE FILE # AS FILE EXTENSION
3150    FORMAT(I3)
C
        IF (FIL(IP) .EQ. ' ') FIL(IP) = '0'    !REPLACE WITH ZERO IF SPACE
        IF (FIL(IP+1) .EQ. ' ') FIL(IP+1) = '0' !REPLACE WITH ZERO IF SPACE
        FIL(IP+3) = 0
C
        RETURN
        END
        SUBROUTINE
     DPDSPD(IGP,NTYPE,IPASS,CFR,DPAMP,RNOISE,DBSPL,ISV,PFIL)
C
        BYTE PFIL(10)
```

```
C
C ..........................................................
      SUBR. STARTS
C
C
      IF (IGP) GO TO 530        !SKIP IF GRAPH MODE
C
      WRITE (5,510) CFR,DBSPL,DPAMP,RNOISE,PFIL
510   FORMAT  (/1X,4(' ',F7.3),' ',10A1)
      RETURN
C
530   IF (NTYPE) GO TO 700
C
      CALL DPIOPL(0,CFR,DBSPL,DPAMP,RNOISE,IPASS)
      RETURN
C
700   CALL DPARPL(0,CFR,DBSPL,DPAMP,RNOISE,IPASS,ISV)
C
      RETURN
      END
      SUBROUTINE  DPIOEX(NTYPE,ICOR,IGP,NBRAVG,SPAN,CRIT,CTLFIL,PFIL)
C
      BYTE  PTB(20),RIT(20)
      BYTE  WRBF(150),PFIL(10),WDAT(19),EB
      BYTE  IDATE(9),SETNAM(6),OLDSET(6),CTLFIL(11)
      BYTE  CORFIL(11),GRFILE(11),XFRFIL(16),RTYPE,NFR,PRSW,GRD,SJT,AFT
C
      DIMENSION CFRB(50)
      DIMENSION  CFRO(4),DBO(4),DPO(4),RNO(4)
C
      COMMON /COM001/ CORFIL,GRFILE,XFRFIL,RTYPE,NFR,PRSW,GRD,SJT,AFT
      COMMON /COM002/ ILOG,LR,IYA,XLO,YLO,XHI,YHI,AX,XLN,XSCALE,YLN,YSCALE
      COMMON /COM003/ DPKHZ,FAKHZ,FAATTN,FBKHZ,FBATTN,DBSPL,STZ,STP,TDB
      COMMON /COM004/ CFRO,DBO,DPO,RNO
      COMMON /COM006/ RNOISE,DPAMP
      COMMON /COM009/ IPTB,IRIT,PTB,RIT
      COMMON /COM010/ SETNAM,OLDSET
C
C ..........................................................
      SUBR. STARTS
C
C
C     GO GET CORRECTION FACTOR DATA OR DPKHZ DATA TO WRITE AS A LINE
C     INTO XFR FILE.
C
      IYA = 40    !Y ADJUST FOR PLOT
      IEOF = 0    !CLEAR END OF FILE FOR CONTROL FILE
      ISK = 1     !NO LINE SKIP FOR 1ST SET OF DATA
      EB = 'E'
```

```
        LENTST = 0
C
        CALL CFRKHZ(ICOR,XFRFIL,CTLFIL,CORFIL,WRBF)
C
        IF (PRSW .EQ. 'Y') CALL DPPRNT(1,NTYPE,CFR,DBSPL,DPAMP,RNOISE,PFIL)
        IF (IGP) CALL GPFPRM(NTYPE,GRFILE)  !READ GRAPH PARAMS
C
        ICC = 0                !^C FLAG
        CALL SCCA(ICC)
        CALL IPOKE("44, IPEEK("44) .OR. "050100)
C
10      KEY = ITTINR()         !FLUSH ANY PREV. KEYS
        IF (KEY .GE. 0) GO TO 10
C
C................................................................
..
C       TARGET FOR DP MAIN LOOP
C
100     CDB = 0.0              !PRE-SET dB CORRECTION TO 0.0
C
        IF (ICOR) READ (3,150,END=3000) CFR,CDB   !READ CORRECTION FACTORS
150     FORMAT(2F9.3)
C
        CALL RDCNFL(2,IEOF,NBRAVG,SPAN,CRIT) !READ CONTROL DATA
        IF (IEOF) GO TO 3000           !OUT, IF EOF
        IF (.NOT. (LENLN)) WRITE (1,160) INT(DBSPL),9,INT(STZ),9,INT(TDB)
160     FORMAT(I3,1A1,I3,1A1,I3)
        LENLN = 1
C
        IF (.NOT. (ICOR)) CFR = DPKHZ  ! CFR = VAL. FROM COR FILE OR DPKHZ
        IF (PRSW .EQ. 'Y') CALL DPPRNT(3,NTYPE,CFR,DBSPL,DPAMP,RNOISE,PFIL)
        IF (.NOT. (IGP)) GO TO 300     !SKIP IF NO GRAPH PARAM. FILE
C
C       MAKE PLOT AXIS, TICS, LABELS, ETC.
C
        CALL DPIOP(NTYPE)
        CALL TCPPLT(1,450,300)
        WRITE (5,200) 31,PFIL
200     FORMAT(1X,10A1,$)
        CALL TCPPLT(1,450,240)
        WRITE (5,3670) 31,(PTB(J),J=1,IPTB)
        CALL TCPPLT(1,450,220)
        WRITE (5,3670) 31,(RIT(J),J=1,IRIT)
C
C Set analyzer to set-up for this run.
C
300     CALL SNDSET(NBRAVG,SPAN)       !SIGNAL ANAL. SETUP
C
        IPASS = 0                      !CLEAR PASSES
        LOOPN = INT((DBSPL - TDB) / STZ) + 1 !CALC. LOOP STEPS
```

```
C
        DO 1000 I = 1,LOOPN      !LOOP THRU dB STEPS
        KEY = ITTINR()           !READ KEYBOARD
        IF (KEY .EQ. 3) GO TO 2000    !LEAVE LOOP IF ^C
C
C       GET DPAMP, RNOISE, CHECK NOISE FLOOR REJECTION.
C       GRAPH AND OR DISPLAY DATA.
C
        CALL NSFLRJ(TN,CRIT,CDB,IPASS,NFR)
        CALL DPDSPD(IGP,NTYPE,IPASS,CFR,DPAMP,RNOISE,DBSPL,ISV,PFIL)
C
        IF (PRSW .EQ. 'Y') CALL DPPRNT(4,NTYPE,CFR,DBSPL,DPAMP,RNOISE,PFIL)
C
        IPASS = 1                !PASS COMPLETED
C
C       Write out the DPAMP value, paired with DPKHZ
C
        CALL INSERT('              ',WDAT,1,19)
        ENCODE (3,650,WDAT(1)) INT(DBSPL)
650     FORMAT(I3)
C
        WDAT(4) = 9
        ENCODE (7,700,WDAT(5)) DPAMP
        WDAT(12) = 9
        ENCODE (7,700,WDAT(13)) RNOISE
700     FORMAT(F7.3)
C
C
        IF (ISK) WRITE (1,750) WDAT
        IF (.NOT. (ISK)) WRITE (1,755) EB,WDAT
750     FORMAT(19A1)
755     FORMAT(1A1/19A1)
        ISK = 1
C
C Calculate next attenuation, applying DB step size.  Ensure also that
C dBattn has not reached max and that DPAMP is still above the noise level.
C
        IF (STP .EQ. 0.0) GO TO 800
C
        IF (DPAMP .LT. (RNOISE + STP)) GO TO 2000   !BASE LIMIT CHECK
C
800     FAATTN = FAATTN + STZ           !ADJUST FOR NEXT PASS
        IF (FAATTN .GT. 80.0) GO TO 2000
        FBATTN = FBATTN + STZ
        IF (FBATTN .GT. 80.0) GO TO 2000
        DBSPL = DBSPL - STZ
C
1000    CONTINUE
C
2000    CALL HPCHAN ('B')        ! ^C^C OR STEP LOOP TARGET
        CALL HPATTN (80.0)
```

```
        CALL HPFREQ (30.0)
        CALL HPCHAN ('A')
        CALL HPATTN (80.0)
        CALL HPFREQ (30.0)
        KSV = KEY
C
        IF (IGP) WRITE (5,2100) 27,12      !ERASE GRAPH SCREEN
2100    FORMAT(1X,2A1)
C
        ISK = 0
        IF (KSV .NE. 3) GO TO 100
C
3000    CALL HPCHAN ('B')          ! END OF FILE/TEST TARGET
        CALL HPATTN (80.0)
        CALL HPFREQ (30.0)
        CALL HPCHAN ('A')
        CALL HPATTN (80.0)
        CALL HPFREQ (30.0)
C
        WRITE (1,3020) EB
3020    FORMAT(1A1/)
C
        CALL CLOSE (1)
        CALL CLOSE (2)
        IF (ICOR) CALL CLOSE(3)
        IF (IGP) CALL CLOSE (4)
3010    KEY = ITTINR()         !FLUSH ANY PREV. KEYS
        IF (KEY .GE. 0) GO TO 3010
        CALL IPOKE("44,IPEEK("44) .AND. (.NOT. "050100))
        CALL SCCA
C
        IF (KSV .NE. 3) GO TO 3160
        IF (AFT .NE. 'Y') GO TO 5100
C
        WRITE (5,3050) 24
3050    FORMAT(/$1X,1A1,'DO FILE TRANSFER TO MAC AS SELECTED? [N/Y]: ')
C
        READ (5,3100) AFT
3100    FORMAT(1A1)
C
        GO TO 5100
C
3160    IF (.NOT. (IGP)) GO TO 5100
        IF (GRD .EQ. 'N') GO TO 5100
C
        CALL DATE(IDATE)
        CALL GPFPRM(NTYPE,GRFILE)
        CALL ASSIGN(1,XFRFIL)
        READ (1,3100) WDAT(1)      !READ PAST INITIAL FILE INFO
        READ (1,3100) WDAT(1)
        READ (1,3100) WDAT(1)
```

```
         READ (1,3100) WDAT(1)
         READ (1,3100) WDAT(1)
         READ (1,3200) N,WRBF     !GET KHZ LINE FROM FILE
3200  FORMAT(Q,150A1)
         READ (1,3100) WDAT(1)
C
         IP = 1
         IP1 = 1
C
3300  DECODE (7,700,WRBF(IP1)) CFRB(IP)  !DECODE KHZ INTO CFR BUFFER
         IP1 = IP1 + 6
         IF (WRBF(IP1) .EQ. ' ') GO TO 3400 !SKIP IF AT END
         IP1 = IP1 + 1
         IP = IP + 1
         GO TO 3300
C
3400  IP1 = 1
C
3500  WRITE (5,2100) 27,12      !ERASE GRAPH SCREEN
C
3600  IPASS = 0
C
         CALL DPIOP(NTYPE)         !SET UP GRAPH
         CALL TCPPLT(1,450,300)     !PUT DATE ON GRAPH
         WRITE (5,3650) 31,IDATE
3650  FORMAT(1X,1A1,9A1,$)
         CALL TCPPLT(1,450,280)     !PUT FREQ. ON GRAPH
         WRITE (5,3660) 31,CFRB(IP1)
3660  FORMAT(1X,1A1,F6.3,' KHZ',$)
         CALL TCPPLT(1,450,260)     !PUT FILE NAME ON GRAPH
         WRITE (5,200) 31,PFIL
         CALL TCPPLT(1,450,240)
         WRITE (5,3670) 31,(PTB(J),J=1,IPTB)
3670  FORMAT(1X,1A1,20A1)
         CALL TCPPLT(1,450,220)
         WRITE (5,3670) 31,(RIT(J),J=1,IRIT)
C
3700  READ (1,750,END=3800) WDAT   !READ FILE DATA
         IF (WDAT(1) .EQ. 'E') GO TO 3800
         DECODE (3,650,WDAT(1)) IDB
         DECODE (7,700,WDAT(5)) DPAMP
         DECODE (7,700,WDAT(13)) RNOISE
         DBSPL = FLOAT(IDB)
C
         CALL DPIOPL(1,CFRB(IP1),DBSPL,DPAMP,RNOISE,IPASS) !PLOT IT
         IPASS = 1
         GO TO 3700
C
3800  WRITE (5,3900) 27,23      !SEND GRAPH TO PRINTER
3900  FORMAT(1X,2A1)
C
```

```
        IP1 = IP1 + 1
        IF (IP1 .LE. IP) GO TO 3500
C
4000    CALL CLOSE (1)
        CALL CLOSE (3)
        CALL CLOSE (4)
C
5100    CALL TEKOUT(24)
C
        RETURN
        END
        SUBROUTINE  DPIOP(NTYPE)
C
C       PLOT AXIS, TICS, LABELS, ETC. FOR I/O DP'S
C
C       ............................................................
C       SUBR STARTS
C
        ITITLE = 1    !PUT TITLES ON PLOT
        IFRL = 1      !LABEL TIC MARKS
C
        CALL DPPLT1(NTYPE,ITITLE,IFRL)  !SET UP GRAPH
        WRITE (5,200) 27,97             !DOTTED GRAPH LINES
200     FORMAT(1X,2A1,$)
C
        DO 250 I = 1,4          !GRAPH ST. DEV. LINES
        IBP = 1
        CALL DPPLT2(IBP,IPERR)
250     CONTINUE
C
        WRITE (5,200) 27,96     !RESTORE TO SOLID LINES
        RETURN
        END
        SUBROUTINE  DPIOPL(IPL,CFR,DBSPL,DPAMP,RNOISE,IPASS)
C
        DIMENSION  CFRO(4),DBO(4),DPO(4),RNO(4)
C
        COMMON /COM002/ ILOG,LR,IYA,XLO,YLO,XHI,YHI,AX,XLN,XSCALE,YLN,YSCALE
        COMMON /COM004/ CFRO,DBO,DPO,RNO
C
C       ............................................................
C       SUBR. STARTS
C
        IX = 375           IMAX X = 325
        IY = 60            IY OFFSET BY 60
C
        IF (IPL) GO TO 400
C
        WRITE (5,200) 31,27,127    !ERASE SEQ. FOR MAC
```

17

```
200     FORMAT(1X,3A1,$)
C
        CALL TCPPLT(1,IX,IY)        !ERASE PREV. TEXT
        WRITE (5,300) 31,CFRO(1),DBO(1),DPO(1),RNO(1)  !REWRITE = ERASE
300     FORMAT (1X,1A1,4(' ',F7.3))
C
        CALL TEKOUT(13)
C
        CALL TCPPLT(1,IX,IY)
        WRITE (5,300) 31,CFR,DBSPL,DPAMP,RNOISE
C
400     IBP = 1
        IF (IPASS) IBP = 2
        IF (IPASS) CALL PLTLIN(1,1,IX,IY,1,DBO(1),DPO(1))
        CALL PLTLIN(1,1,IX,IY,IBP,DBSPL,DPAMP)
        CALL PLTCRS(IX,IY,2)
        IF (IPASS) CALL PLTLIN(1,1,IX,IY,1,DBO(1),RNO(1))
        CALL PLTLIN(1,1,IX,IY,IBP,DBSPL,RNOISE)
C
        CFRO(1) = CFR               !UPDATE AS PREV. INFO
        DBO(1) = DBSPL
        DPO(1) = DPAMP
        RNO(1) = RNOISE
C
        RETURN
        END
        SUBROUTINE  DPNERR(ISW,IERR,DPKHZ,DPAMP,RNOISE)
C
        BYTE MMKCMD(19)   !"Move marker" command to the analyzer.
        BYTE MKRVAL(54)   !Marker values, as read from the analyzer.
C                         !to confirm there was no error in conversion.
C
C
*******************************************
* * *
C     SUBR. STARTS
C
C ISW = 0 Set the marker to DPkhz and read its amplitude OR
C ISW = 1 Set the marker to DPkhz+50hz to get noise floor amplitude
C
        IERR = 0
        DPT = DPKHZ * 1000.0
        IF (ISW) DPT = DPT+ 50.0
        ENCODE (18, 100, MMKCMD) DPT
100     FORMAT ('MMKP ', F9.3, ' HZ;')
C
105     J = IBUP (0, 16, MMKCMD, 18)
C
C       Read the amplitude.
C
        J = IBUP (0, 16, 'RDMK;', 5)       !Request the marker values.
```

```
         J = IBUP (1, 16, MKRVAL, 54)      !Read the marker values.
C
110      J = IBUP (6, 16)                  !Poll the analyzer.
         IF (J .AND. 32) GO TO 200
         IF (J .AND. 17) GO TO 111
         GO TO 110
C
111      DECODE (16, 115, MKRVAL(22),ERR=300) DPT
115      FORMAT (E16.3)
         GO TO 500
C
200      J = IBUP (0, 16, 'ERR?;', 5)
         GO TO 105
C
C We have detected that invalid data has been received from the analyzer.
C
300      IERR = 1
C
         WRITE  (5,410)  24,(MKRVAL(J),J=22,37),DPT,7,7
410      FORMAT (/1X,1A1,'ERROR ',16A1,' ',F9.2,2A1)
         RETURN
C
500      IF (DPT .LT. -99.999 .OR. DPT .GT. 999.999) IERR = 1
C
         IF (IERR) WRITE (5,510)  24,(MKRVAL(J),J=22,37),7,7
510      FORMAT(1X,1A1,'MARKER ERROR, VALUE = ',16A1,2A1)
C
         IF (.NOT. (ISW)) DPAMP = DPT
         IF (ISW) RNOISE = DPT
C
         RETURN
         END
         SUBROUTINE  DPPLT1(NTYPE,ITITLE,IFRL)
C
         BYTE XSTR(23),YSTR(20)
C
         COMMON /COM002/ ILOG,LR,IYA,XLO,YLO,XHI,YHI,AX,XLN,XSCALE,YLN,YSCALE
         COMMON /COM005/ XINC,XLBINC,YINC,YLBINC
C
         DATA YSTR /' ','D','P',' ','A','M','P','L','I','T','U','D','E',
        +           ' ','d','B',' ','S','P','L'/
C
C        ................................................................
C        SUBR. STARTS
C
C        PLOT X/Y AXIS
C
         CALL PLAXIS               !GO PLOT X/Y AXIS
C
         IF (.NOT. (ILOG)) GO TO 50
         CALL LBLXLG(IFRL)
```

```
         GO TO 500
C
50       X = XLO              !START WITH 1ST X...
         Y = YLO              !...AND Y
         X1 = XLO             !SAVE 1ST TIC LOCATION
C
C        PLOT X TICS, LABELS
C
100      CALL PLTLIN(1,1,IX,IY,1,X,Y)         !INIT PLOT CURSOR
         IYM = IY - 5                         !EXTEND Y FOR TIC
         IX1 = INT(X * 10.0)
         IX2 = INT(X1 * 10.0)
         IF (IX1 .EQ. IX2) IYM = IYM - 5   !EXTEND TIC FOR LABEL
         CALL TCPPLT(2,IX,IYM)                !PLOT LINE
         IF (IX1 .NE. IX2) GO TO 450    !SKIP IF NO LABEL
         IF (IFRL .EQ. 0) GO TO 400     !SKIP IF NO LABEL
         IYM = IYM - 10                       !ELSE, CURSOR DOWN...
         IXM = IX - 10                        !...AND LEFT
         CALL TCPPLT(1,IXM,IYM)               !POSITION CURSOR
         IX3 = MOD(IX1,10)
         IF (.NOT. (IX3)) WRITE (5,200) 31,INT(X)
         IF (IX3) WRITE (5,210) 31,X
200      FORMAT(1X,1A1,I3)
210      FORMAT(1X,1A1,F3.1)
C
400      X1 = X1 + XLBINC                !BUMP TIC INCRE.
C
450      X = X + XINC                    !BUMP X INCRE.
         IF (X .LE. XHI) GO TO 100       !LOOP 'TIL END
C
C        X TITLE
C
500      CALL  TCPPLT(1,100,8)
C
         IF (.NOT. (ITITLE)) GO TO 520
         IF (NTYPE .EQ. 0) CALL INSERT ('PRIMARY LEVELS (dB SPL)',XSTR,1,23)
         IF (NTYPE .EQ. 1) CALL INSERT ('    FREQ. (KHZ)        ',XSTR,1,23)
         IF (NTYPE .EQ. 2) CALL INSERT ('    F2/F1 RATIO        ',XSTR,1,23)
C
         WRITE (5,510) 31,XSTR           !WRITE TITLE
510      FORMAT(1X,1A1,23A1)
C
C        PLOT Y TICS, LABELS
C
520      X = XLO        !SAME COMMENTS AS ABOVE (EXCEPT FOR LOG)
         Y = YLO
         Y1 = YLO
C
550      CALL  PLTLIN(1,1,IX,IY,1,X,Y)
         IXM = IX - 5
         IF (Y .EQ. Y1) IXM = IXM - 5
```

```
        CALL TCPPLT(2,IXM,IY)
        IF (Y .NE. Y1) GO TO 700
        IXM = IXM - 25
        IYM = IY - 5
        CALL TCPPLT(1,IXM,IYM)
        WRITE (5,600) 31,INT(Y)
600     FORMAT(1X,1A1,I3)
        Y1 = Y1 + YLBINC
C
700     Y = Y + YINC
        IF (Y .LE. YHI) GO TO 550
C
        IF (.NOT. (ITITLE)) RETURN
        IY = 300
C
        DO 800 I = 1,20        !PRINT CHARACTERS VERTICALLY
        CALL TCPPLT(1,8,IY)    !TOP OF THE TITLE
        WRITE (5,750) 31,YSTR(I)
750     FORMAT(1X,1A1,1A1)
        IY = IY - 10
800     CONTINUE
C
        RETURN
        END
        SUBROUTINE  DPPLT2(IBP,IPERR)
C
C       .................................................
C
C       SUBR. STARTS
C
        IPERR = 0
C
100     READ (4,200,ERR=100,END=300) X,Y  !READ ST.DEV DATA
200     FORMAT(2F9.3)
C
        IF (X .EQ. 0.0 .AND. Y .EQ. 0.0) GO TO 100
C
        IF (X .EQ. 999.0) RETURN       !END OF DATA TEST
        CALL PLTLIN(1,1,IX,IY,IBP,X,Y) !PLOT THE DATA
        IBP = 2                        !DON'T INIT PLOT ANYMORE
        GO TO 100                      !LOOP FOR MORE DATA
C
300     IPERR = 1
        RETURN
        END
        SUBROUTINE  DPPPRM(NTYPE,CRIT,NBRAVG,SPAN,STP,IGP,ICOR)
C
        BYTE SP
        BYTE CORFIL(11),GRFILE(11),XFRFIL(16),RTYPE,NFR,PRSW,GRD,SJT,AFT
C
        COMMON /COM001/ CORFIL,GRFILE,XFRFIL,RTYPE,NFR,PRSW,GRD,SJT,AFT
C
```

```
C...........................................................
.
C     SUBR. STARTS
C
      SP = ' '
      CALL SCFUNC(1,N,N)      !CLEAR SCREEN
      CALL SCFUNC(3,2,1)      !POSN. CURSOR LINE 2, COL 1
      WRITE (5,20)
20    FORMAT(1X,'DEFAULT SETTINGS - AT THE "ENTER OPTION" PROMPT:'/1X,
     + 'SELECT A LETTER IN THE OPTION COLUMN TO CHANGE A DEFAULT SETTING.'/)
C
      WRITE (5,100) NBRAVG,SPAN,PRSW,CORFIL,GRFILE,NFR,CRIT,GRD,STP,
     + SJT,AFT,RTYPE
100   FORMAT(1X,
     + 'OPTION  SETTING   FUNCTION'/1X,
     +         '------  -------   ----------------------------------'/1X,
     + ' A ',I6,'      NUMBER OF SIGNAL ANALYZER AVERAGES'/1X,
     + ' F ',F7.3,' kHz  FREQUENCY SPAN OF ANALYZER WINDOW'/1X,
     + ' P  ',1A1,'       ECHO SCREEN TO PRINTER'/1X,
     + ' D ',11A1,'  DPE AMPLITUDE CORRECTION FILE'/1X,
     + ' G ',11A1,'  GRAPH PARAMETER AND AV. +- STDEV FILE'/1X,
     + ' N  ',1A1,'       USE NOISE FLOOR REJECTION SUBROUTINE'/1X,
     + ' C ',F7.3,'     NOISE FLOOR REJECTION CRITERION'/1X,
     + ' M  ',1A1,'       DUMP GRAPHICS AT END OF RUN'/1X,
     + ' S ',F7.3,'    DP AMP/NF DIFFERENCE STOP POINT'/1X,
     + ' B  ',1A1,'       SUBJECT TYPE'/1X,
     + ' T  ',1A1,'       AUTO TRANSFER TO MACINTOSH'/1X,
     + ' R  ',1A1,'       RUN TYPE'//1X,
     + ' X           EXIT MENU, CONTINUE WITH RUN'//$1X,
     + 'ENTER OPTION:')
C
120   CALL SCFUNC(3,22,15)
C
      WRITE (5,130) 27       !WAS SPACE @ 350
130   FORMAT(1X,1A1,'[J',$)
C     CALL SCFUNC(3,22,15)
      CALL IPOKE("44, IPEEK("44) .OR. "050100)
C
150   KEY = ITTINR()         !FLUSH ANY PREV. KEYS
      IF (KEY .GE. 0) GO TO 150
C
200   KEY = ITTINR()         !READ KEYBOARD
      IF (KEY .LT. 0) GO TO 200   !LOOP IF NO INPUT
C
      KEY = KEY .AND. "177
      IF (KEY .GT. 90) KEY = KEY - 32
      CALL IPOKE("44,IPEEK("44) .AND. (.NOT. "050100))
C
      IF (KEY .EQ. 88) GO TO 9000
      IF (KEY .LT. 65 .OR. KEY .GT. 84) GO TO 8000
```

22

```
C
300   CALL SCFUNC(3,22,15)
C
      WRITE (5,350) KEY
350   FORMAT(1X,1A1,$)
C
      CALL SCFUNC(3,23,1)
      WRITE (5,400) 27
400   FORMAT(1X,1A1,'[0J',$)
      CALL SCFUNC(3,23,1)
C
      KEY = KEY - 64
      CALL SCFUNC(3,22,21)
C
C         A   B   C   D   E   F   G   H   I   J   K
      GO  TO  (1000,1100,1200,1520,8000,1500,1600,8000,8000,8000,8000,
     +         8000,1900,2000,8000,2100,8000,2400,1280,2300) KEY
C         L   M   N   O   P   Q   R   S   T
C
1000  WRITE (5,1010)
1010  FORMAT(1X,'ENTER VALUE : '$)
C
      READ (5,1050) NBRAVG
1050  FORMAT(I6)
C
      CALL SCFUNC(3,7,7)
      WRITE (5,1060) NBRAVG
1060  FORMAT(1X,I6,$)
      GO TO 120
C
1100  WRITE (5,1110)
1110  FORMAT(1X,'ENTER SUBJECT TYPE:'$)
C
      READ (5,1120) SJT
1120  FORMAT(1A1)
C
      CALL SCFUNC(3,16,12)
      WRITE (5,1150) SJT
1150  FORMAT(1X,1A1,$)
      GO TO 120
C
1200  WRITE (5,1010)
C
      READ (5,1250) CRIT
1250  FORMAT(F10.0)
C
      CALL SCFUNC(3,13,7)
      WRITE (5,1260) CRIT
1260  FORMAT(1X,F7.3,$)
      GO TO 120
C
```

```
1280  WRITE (5,1010)
C
      READ (5,1250) STP
C
      CALL SCFUNC(3,15,7)
      WRITE (5,1260) STP
      GO TO 120
C
1500  WRITE (5,1010)
C
      READ (5,1250) SPAN
C
      CALL SCFUNC(3,8,7)
      WRITE (5,1260) SPAN
      GO TO 120
C
1520  WRITE (5,1610)
C
      READ (5,1620) CORFIL
C
      ICOR = 1
      CALL FILXST(IX,CORFIL)
      IF (IX .GT. 0) GO TO 1540
      ICOR = 0
      CALL TEKOUT(7)
      CALL INSERT ('NO FILE   ',CORFIL,1,11)
C
1540  CALL SCFUNC(3,10,7)
      WRITE (5,1660) CORFIL
      GO TO 120
C
1600  WRITE (5,1610)
1610  FORMAT(1X,'ENTER FILE: ',$)
C
      READ (5,1620) GRFILE
1620  FORMAT(11A1)
C
      IGP = 1
      CALL FILXST(IX,GRFILE)
      IF (IX .GT. 0) GO TO 1640
      IGP = 0
      CALL TEKOUT(7)
      CALL INSERT ('NO FILE   ',GRFILE,1,11)
C
1640  CALL SCFUNC(3,11,7)
      WRITE (5,1660) GRFILE
1660  FORMAT(1X,11A1,$)
      GO TO 120
C
1900  IF (GRD .EQ. 'Y') GO TO 1910
      GRD = 'Y'
```

24

```
              GO TO 1920
C
1910    GRD = 'N'
C
1920    CALL SCFUNC(3,14,12)
        WRITE (5,1150) GRD
        GO TO 120
C
2000    IF (NFR .EQ. 'Y') GO TO 2010
        NFR = 'Y'
        GO TO 2020
C
2010    NFR = 'N'
C
2020    CALL SCFUNC(3,12,12)
        WRITE (5,1150) NFR
        GO TO 120
C
2100    IF (PRSW .EQ. 'Y') GO TO 2110
        PRSW = 'Y'
        GO TO 2120
C
2110    PRSW = 'N'
C
2120    CALL SCFUNC(3,9,12)
        WRITE (5,1150) PRSW
        GO TO 120
C
2300    IF (AFT .EQ. 'Y') GO TO 2310
        AFT = 'Y'
        GO TO 2320
C
2310    AFT = 'N'
C
2320    CALL SCFUNC(3,17,12)
        WRITE (5,1150) AFT
        GO TO 120
C
2400    WRITE  (5,2410)
2410    FORMAT(1X,'ENTER RUN TYPE: '$)
C
        READ  (5,1120) RTYPE
C
        CALL SCFUNC(3,18,12)
        WRITE (5,1150) RTYPE
        GO TO 120
C
8000    CALL TEKOUT(7)
        CALL SCFUNC(3,22,15)
        WRITE (5,350) SP
        GO TO 120
```

```
C
9000    RETURN
        END
        SUBROUTINE  DPPRNT(IPF,NTYPE,CFR,DBSPL,DPAMP,RNOISE,PFIL)
C
        BYTE PTB(20),RIT(20)
        BYTE IDATE(9),PFIL(10)
C
        COMMON /COM009/ IPTB,IRIT,PTB,RIT
C
C       ............................................................
C       SUBR. STARTS
C
        OPEN (UNIT=6, NAME='LP:', CARRIAGECONTROL='FORTRAN')
C
        GO TO (100,200,300,400,500) IPF
C
C       IPF = 1...FORM FEED AND DATE
C
100     CALL DATE(IDATE)        !GET THE DATE
C
        WRITE (6,105) 12,IDATE
        WRITE (6,110) PFIL
105     FORMAT(1X,1A1,'DATE : ',9A1)
110     FORMAT(1X,'FILE : ',10A1)
C
        WRITE (6,120) (PTB(J),J=1,IPTB)
        WRITE (6,130) (RIT(J),J=1,IRIT)
120     FORMAT(1X,'TITLE : ',20A1)
130     FORMAT(1X,'RUN ID: ',20A1/)
C
        GO TO 1000
C
C       IPF = 2...HEADER FOR A OR R TYPES
C
200     IF (NTYPE .EQ. 1) WRITE (6,210)
        IF (NTYPE .EQ. 2) WRITE (6,220)
210     FORMAT(/1X,'  FREQ.    dBSPL    DP AMP.   NS. AMP.')
220     FORMAT(/1X,'  RATIO    dBSPL    DP AMP.   NS. AMP.')
        GO TO 1000
C
C       IPF = 3...HEADER FOR I/O TYPE
C
300     WRITE (6,310) CFR
310     FORMAT(/1X,F9.3,' KHZ     DP AMP      NS AMP')
        GO TO 1000
C
C       IPF = 4...DATA FOR I/O TYPE
C
400     WRITE (6,410) DBSPL,DPAMP,RNOISE
410     FORMAT('+',T5,F6.2,T22,F6.2,T37,F6.2)
```

26

```
        GO TO 1000
C
C       IPF = 5...DATA FOR A OR R TYPE
C
500     WRITE (6,510) CFR,DBSPL,DPAMP,RNOISE
510     FORMAT('+',F9.3,T16,F6.2,T28,F6.2,T41,F6.2)
C
1000    CLOSE (UNIT=6)
C
        RETURN
        END
        SUBROUTINE DPSYN
C
        COMMON /COM003/ DPKHZ,FAKHZ,FAATTN,FBKHZ,FBATTN
        COMMON /COM006/ RNOISE,DPAMP
C
C
*************************************************************
*******
C       SUBR. STARTS
C
C       Set synthesizer frequency, attenuation
C
400     CALL HPCHAN ('A')
        CALL HPATTN (FAATTN)           !for channel A;
        CALL HPCHAN ('B')
        CALL HPATTN (FBATTN)           !for channel B.
C
C Initiate an averaged measurement of the signal at the analyzer
C and wait for average to be complete.
C
        J = IBUP (0, 16, 'RSRQ; STRT; ERR?;', 17)
C
450     J = IBUP (6, 16)               !Poll the analyzer.
        IF ((J.AND.001).EQ..FALSE.) GO TO 450    !LOOP 'TILL FINISHED
C
C Get the marker values for both DPAMP and the NOISE floor.
C
        CALL DPNERR(0,IERR,DPKHZ,DPAMP,RNOISE)
        IF (IERR) GO TO 400
        CALL DPNERR(1,IERR,DPKHZ,DPAMP,RNOISE)
        IF (IERR) GO TO 400
C
        RETURN
        END
        SUBROUTINE DPVERF(IFN,FIL)
C
C       SEARCHES BY 10'S, THEN BY 1'S (VIA FILE EXTENSION NUMBER),
C       FOR THE NEXT AVAILABLE FILE EXTENSION NUMBER.
C
        BYTE FIL(16)
```

```
C
C ............................................................
..
C
      IFN = 11        !START AT FILE EXTENSION 11
      INC = 10        !SEARCH BY 10'S
      IRET = 1        !RETURN TO 50
      GO TO 100
C
50    INC = 1         !NOW, SEARCH BY 1'S
      IFN = IFN - 10  !ADJUST FILE NUMBER
      IRET = 0        !RETURN TO CALLER
C
100   CALL DPCDFX(IFN,FIL)   !ENCODE EXTEN. TO NAME
C
      CALL FILXST(IX,FIL)
      IF (IX .LE. 0) GO TO 200
      IFN = IFN + INC              !YES, KEEP SEARCHING
      GO TO 100
C
200   IF (IRET) GO TO 50
C
      CALL CLOSE (4)
      RETURN
      END
      SUBROUTINE   FILXST(IX,FILE)
C
C ............................................................
.
C      PURPOSE:  VERIFIES THE EXISTENCE OF A FILE SPECIFIED BY
C                THE CALLER.
C
C      INPUTS:  FILE   UP TO 15 BYTES OF A FILE NAME
C      OUTPUTS: IX     NEGATIVE = FILE DOESN'T EXIST
C                      POSITIVE = FILE'S LENGTH IN BLOCKS
C
C
C ............................................................
.
C
      BYTE  FILE(16),TMPBUF(13)
      DIMENSION IAB(6)
C
C ............................................................
.
C     BEGIN
C
C     PREPARE TMPBUF FOR LOOKUP BUFFER. SY IS DEVICE DEFAULT
```

```
C
        CALL INSERT ('SY       ',TMPBUF,1,12) !SET TEMP. BUFFER
        TMPBUF(13) = 0
C
        ICLN = INDEX(FILE,':')   !FIND COLON, IF DEVICE SPECIFIED
        IF (ICLN .GT. 4) ICLN = 0
        IPER = INDEX(FILE,'.')   !FIND EXTENSION PERIOD
C       .........................................
C
C       XFER DEVICE FROM PARAMETER FILE TO TMPBUF
C
        IF (ICLN .EQ. 0) GO TO 10   !SKIP IF NO DEVICE SPECIFIED
        I = ICLN - 1            !DEVICE BYTE LENGTH
        CALL INSERT (FILE,TMPBUF,1,I) !BUFFER XFER
        CALL IRAD50 (3,TMPBUF,IDEV)
        IFF = IFETCH(IDEV)
        IF (IFF) PAUSE 'DEVICE ERROR'
C
C       .........................................
C
C       XFER NAME FROM PARAMETER FILE TO TMPBUF
C
10      I = ICLN + 1            !1ST BYTE AFTER DEVICE
        IBOD = IPER - I         !FILE BODY NAME LENGTH
        CALL INSERT (FILE(I),TMPBUF,4,IBOD)
C
C       .........................................
C
C       XFER EXTENSION FROM PARAMETER FILE TO TMPBUF
C
        I = IPER + 1
        CALL INSERT (FILE(I),TMPBUF,10,3)  !FILE EXTENSION
C
C       RADIX TMPBUF, LOOKUP FILE
C
        CALL IRAD50 (12,TMPBUF,IAB)
        ICH = IGETC()           !GET A CHANNEL
        IX = LOOKUP(ICH,IAB)    !LOOK UP FILE
        CALL ICLOSE (ICH,I)
        CALL IFREEC(ICH)        !FREE THE CHANNEL
C
        RETURN
        END
        SUBROUTINE GPFPRM(NTYPE,GPFFIL)
C
        BYTE BLOG,CLRG(2),CLRS(4),GPFFIL(11)
C
        COMMON /COM002/ ILOG,LR,IYA,XLO,YLO,XHI,YHI,AX,XLN,XSCALE,YLN,YSCALE
        COMMON /COM005/ XINC,XLBINC,YINC,YLBINC
C
        DATA CLRG /27,12/                   !CLEAR GRAPH
        DATA CLRS /27,'[','2','J'/
C
```

29

```
C
..................................................................
........
C       SUBR. STARTS
C
        WRITE (5,5) CLRS,CLRG   !CLEAR SCREEN, GRAPH
5       FORMAT(1X,4A1,2A1)
C
C       NTYPE = 0 FOR "I" TYPE GPF FILES.
C
        XLN = 300.0             !X LENGTH IN PIXELS
        YLN = 300.0             !Y LENGTH
        IF (.NOT. (NTYPE)) GO TO 10
        XLN = 300.0             !"A" OR "R" TYPE FILES
        YLN = 135.0
C
10      CALL ASSIGN(4,GPFFIL)
        READ (4,20) BLOG        !LOG. FLAG
20      FORMAT(1A1)
C
        ILOG = 0
        IF (BLOG .EQ. 'Y') ILOG = 1
C
        READ(4,50)XLO           !LEAST X
        READ(4,50)XHI           !MOST X
        READ(4,50)YLO           !SAME FOR Y'S
        READ(4,50)YHI
        YSCALE = YHI - YLO      !Y PLOT SCALE
        IF(ILOG) GO TO 30       !SKIP XTICS & LABELS IF IN LOG SCALE
        AX = XLO                !ELSE, XLO NOT LOG
        XSCALE = XHI - AX       !NEITHER IS XSCALE
        READ(4,50)XINC          !TIC INCREMENT
        READ(4,50)XLBINC        !LABEL INCREMENT
        XST = XSCALE / XLBINC   !HOW MANY TICS
        GO TO 40
C
30      IF (.NOT. (NTYPE)) GO TO 35
        XLO = XLO / 1000.0
        XHI = XHI / 1000.0
C
35      AX = ALOG10(XLO)        !LOG X'S
        XSCALE = ALOG10(XHI) - AX
        XST = 1                 !LOW TICK COUNT
C
40      READ(4,50)YINC          !Y TIC INC.
        READ(4,50)YLBINC        !Y LABEL INC.
50      FORMAT(F7.0)
C
        RETURN
        END
        SUBROUTINE LBLXLG(IFRL)
```

```
C
        COMMON /COM002/ ILOG,LR,IYA,XLO,YLO,XHI,YHI,AX,XLN,XSCALE,YLN,YSCALE
C
C       ............................................................
C       SUBR. STARTS
C
        Y = YLO                  !Y LOW
        XINC = 0.1               !X TIC INCREMENT
        XTIC = 0.1               !START XTIC
        XTGT = 1.0               !X TARGET
        XLBL = XLO               !1ST X LABEL = X LOW
        IXT = INT(XTIC * 10.0)
        IXL = INT(XLBL * 10.0)
        IXTG = INT(XTGT * 10.0)
C
100     IF (IXT .EQ. IXL) GO TO 200    !CLIMBING UP TO X LOW
        XTIC = XTIC + XINC             !NOT YET, INCREMENT X TIC
        IXT = INT(XTIC * 10.0)
        IF (IXT .LT. IXTG) GO TO 100   !REPEAT IF NOT AT X TARGET
        XINC = XINC * 10.0             !ELSE, MAKE NEXT MULT. OF 10
        XTGT = XTGT * 10.0
        IXTG = INT(XTGT * 10.0)
        GO TO 100                !RETRY
C
200     CALL PLTLIN(1,1,IX,IY,1,XTIC,Y)     !TIC LOCATION
        IYM = IY - 5             !Y TARGET FOR TIC
        CALL TCPPLT(2,IX,IYM)              !PLOT TIC
        IF (IXT .NE. IXL) GO TO 600        !SKIP IF NO EXTEND TIC
        IYM = IYM - 5            !EXTEND TIC FOR LABEL
        CALL TCPPLT(2,IX,IYM)              !PLOT IT
        IF (.NOT. (IFRL)) GO TO 600        !SKIP IF NO LABEL
        IYM = IYM - 10           !MOVE CURSOR DOWN...
        IXM = IX - 10            !...AND LEFT
        CALL TCPPLT(1,IXM,IYM)             !POSITION CURSOR
        IF (XTIC .LT. 1.0) WRITE (5,400) 31,XTIC        !DISPLAY X (.N)
        IF (XTIC .GT. 99.0) WRITE (5,500) 31,INT(XTIC)  !       (NN)
        IF (XTIC .GE. 1.0 .AND. XTIC .LT. 100.0) WRITE (5,300) 31,INT(XTIC)
300     FORMAT(1X,1A1,I2,$)
400     FORMAT(1X,1A1,F3.1,$)
500     FORMAT(1X,1A1,I3,$)
C
600     XTIC = XTIC + XINC       !BUMP FOR NEXT TIC
        IXT = INT(XTIC * 10.0)
        IF (XTIC .GT. XHI) RETURN          !END IF PAST X HIGH
        IF (IXT .LT. IXTG) GO TO 700       !SKIP IF NOT AT X TARGET
        XINC = XINC * 10.0                 !ELSE, NEXT MULTIPLE OF 10
        XTGT = XTGT * 10.0
        IXTG = INT(XTGT * 10.0)
C
700     IXTST = INT(XINC * 10.0)
        IF (IXT .EQ. IXTST) XLBL = XTIC
```

```
            IF (IXT .EQ. (2 * IXTST)) XLBL = XTIC
            IF (IXT .EQ. (5 * IXTST)) XLBL = XTIC
            IXL = INT(XLBL * 10.0)
            GO TO 200
C
            END
            SUBROUTINE  MACTIT(XFRFIL,DSPF,RTYPE,SJT)
C
            BYTE  PTB(20),RIT(20),XFRFIL(16),DSPF(10),FNAM(4),EAR,RTYPE,SJT
C
            COMMON /COM009/ IPTB,IRIT,PTB,RIT
C
C
*****************************************************************
C    SUBR STARTS
C
            EAR = ' '
            DO 20 I = 1,20
            PTB(I) = ' '
            RIT(I) = ' '
            IF (I .LT. 5) FNAM(I) = ' '
            IF (I .LT. 11) DSPF(I) = ' '
 20         CONTINUE
C
            CALL SCFUNC(1,N,N)
C
 50         CALL SCFUNC(3,3,0)
            WRITE (5,100)
 100        FORMAT(1X,
           + '1. ENTER PROJECT TITLE (AS IN MAC FOLDER NAME, 20 CHARS MAX):')
C
 150        CALL SCFUNC(3,6,0)
            WRITE (5,200)
 200        FORMAT(1X,'2. ENTER RUN IDENTIFICATION TITLE (20 CHARS MAX):')
C
 250        CALL  SCFUNC(3,9,0)
            WRITE (5,300)
 300        FORMAT(1X,'3. ENTER BASE FILE NAME (4 CHARS. MAX.): ')
C
 350        CALL SCFUNC(3,11,0)
            WRITE (5,400)
 400        FORMAT(1X,'4. ENTER EAR (R OR L): ')
C
            IP = 0
            GO TO 1000
C
 600        GO TO (1000,1100,1200,1300) LP
C
 1000       CALL SCFUNC(3,4,4)
            WRITE (5,1010)
 1010       FORMAT(1X,'_____',$)
```

```
        CALL SCFUNC(3,4,4)
        READ (5,1020) IPTB,PTB
1020    FORMAT(Q,20A1)
C
        IF (IPTB .LT. 21) GO TO 1090
        IPTB = 20
        CALL SCFUNC(3,4,24)
        WRITE (5,1030) 27
1030    FORMAT(1X,1A1,'[K')
C
1090    IF (IP) GO TO 2000
C
1100    CALL SCFUNC(3,7,4)
        WRITE (5,1010)
        CALL SCFUNC(3,7,4)
        READ (5,1020) IRIT,RIT
        IF (IRIT .LT. 21) GO TO 1190
        IRIT = 20
        CALL SCFUNC(3,7,24)
        WRITE (5,1030) 27
C
1190    IF (IP) GO TO 2000
C
1200    CALL SCFUNC(3,9,42)
        WRITE (5,1210)
1210    FORMAT(1X,'____',$)
        CALL SCFUNC(3,9,42)
        READ (5,1220) IFL,FNAM
1220    FORMAT(Q,4A1)
        IF (.NOT. (IFL)) CALL TEKOUT(7)
        IF (.NOT. (IFL)) GO TO 1200
        IF (IP) GO TO 2000
C
1300    CALL SCFUNC(3,11,24)
        WRITE (5,1310)
1310    FORMAT(1X,'_',$)
        CALL SCFUNC(3,11,24)
        READ (5,1320) EAR
1320    FORMAT(1A1)
C
2000    IP = 1
        CALL SCFUNC(3,15,0)
        WRITE (5,2100) 27
2100    FORMAT(1X,1A1,'[J')
C
        CALL SCFUNC(3,15,0)
        WRITE (5,2200)
2200    FORMAT($1X,'CONTINUE? [Y/N]: ')
C
        READ (5,1320) YN
        IF (YN .EQ. 'Y') GO TO 3000
```

```
C
      WRITE (5,2300)
2300  FORMAT(/$1X,'SELECT ENTRY TO CHANGE [1/2/3/4]: ')
C
      READ (5,2400) LP
2400  FORMAT(I1)
C
      GO TO 600
C
3000  CALL INSERT(FNAM,XFRFIL,5,IFL)
      IP = IFL + 5
      XFRFIL(IP) = EAR
      XFRFIL(IP+1) = RTYPE
      XFRFIL(IP+2) = '.'
      CALL DPVERF(I,XFRFIL)
      IP = IFL + 6
      CALL INSERT(XFRFIL(5),DSPF,1,IP)
C
      CALL ASSIGN(1,XFRFIL)
C
      WRITE (1,4000) RTYPE
4000  FORMAT(1A1)
C
      WRITE (1,4000) SJT
C
      WRITE (1,4100) (DSPF(J),J=1,IP)
4100  FORMAT(10A1)
C
      WRITE (1,4200) (PTB(J),J=1,IPTB)
4200  FORMAT(20A1)
C
      WRITE (1,4200) (RIT(J),J=1,IRIT)
C
      RETURN
      END
      SUBROUTINE NSFLRJ(TN,CRIT,CORR,IPASS,NFR)
C
      BYTE NFR
C
      DIMENSION TDPAMP(4),TNFAMP(4)
C
      COMMON /COM006/ RNOISE,DPAMP
C
C
*******************************************************
C     SUBR. STARTS
C
      IF (NFR .EQ. 'Y') GO TO 50
      CALL DPSYN
      DPAMP = DPAMP + CORR
      RNOISE = RNOISE + CORR
```

```
        RETURN
C
50      IF (IPASS) GO TO 200  !SKIP IF NOT INITIAL PASS
C
C       ........................................
C       INITIAL PASS NOISE FLOOR REJECTION
C
        DO 100 I = 1,4       !GET 4 VALUES OF DPAMP & RNOISE
        CALL DPSYN           !GET AMPLITUDES
        TDPAMP(I) = DPAMP    !SAVE DP
        TNFAMP(I) = RNOISE   !SAVE NOISE
100     CONTINUE
C
        GO TO 500            !GO GET SMALLEST NOISE VALUE
C
C       ........................................
C
C       SUBSEQUENT NOISE FLOOR REJECTIONS
C
200     ISV = 1
C
300     CALL DPSYN
        TDPAMP(ISV) = DPAMP    !SAVE DP
        TNFAMP(ISV) = RNOISE   !SAVE NOISE
C
        IF (TNFAMP(ISV) .LT. (TN + CRIT)) GO TO 400 !NOISE VS CRIT TEST
C
C       NOISE TEST FAILURE - RETRY UP TO 4 TIMES FOR A LESSER
C       NOISE VALUE.
C
        IF (ISV .EQ. 4) GO TO 500   !SKIP IF END OF BUFFERS
        ISV = ISV + 1               !ELSE, BUMP POINTER
        GO TO 300                   !RETRY
C
C       LESS THAN 4 RETRY FAILURES - GET LEAST NOISE VALUE WITH
C       CORRESPONDING DPAMP.
C
400     IF (TNFAMP(ISV) .LT. TN) TN = TNFAMP(ISV)
        GO TO 700
C
C       GET LEAST NOISE VALUE WITH CORRESPONDING DPAMP
C
500     ISV = 1
        TN = TNFAMP(1)       !INIT. VALUE WITH 1ST OF 4
C
        DO 600 I = 2,4              !LOOP THRU REST
        IF (TNFAMP(I) .LT. TN) ISV = I   !COMPARE FOR LOWEST
600     CONTINUE
C
        TN = TNFAMP(ISV)            !TNFAMP(ISV) WAS LOWEST
C
```

```
700     DPAMP = TDPAMP(ISV) + CORR
        RNOISE = TNFAMP(ISV) + CORR
C
        RETURN
        END
        SUBROUTINE PLAXIS
C
        COMMON /COM002/ ILOG,LR,IYA,XLO,YLO,XHI,YHI,AX,XLN,XSCALE,YLN,YSCALE
C
C   ...................................................................
C       SUBR. STARTS
C
        X = XLO                     !CURSOR TO XLO,YLO
        Y = YLO
        CALL PLTLIN(1,1,IX,IY,1,X,Y)
C
        IXS = IX
        IYS = IY
        X = XHI                     !LINE TO XHI
        CALL PLTLIN(1,0,IX,IY,2,X,Y)
C
        CALL TCPPLT(1,IXS,IYS)      !CURSOR TO XLO,YLO
        IX = IXS
C
        Y = YHI                     !LINE TO YHI
        CALL PLTLIN(0,1,IX,IY,2,X,Y)
C
        RETURN
        END
        SUBROUTINE PLTCRS(IX,IY,ISIZ)
C
C   ...................................................................
C       SUBR. STARTS
C
C       PLOT A CROSS, +/- 10 OR 3 ON X AND Y
C
        IYP = IY + ISIZ
        IYM = IY - ISIZ
        IXP = IX + ISIZ
        IXM = IX - ISIZ
C
        IF (IXM .LT. 0) IXM = 0
        IF (IXP .LT. 0) IXP = 0
        IF (IYM .LT. 0) IYM = 0
        IF (IYP .LT. 0) IYP = 0
        IF (IYM .GT. 479) IYM = 479
        IF (IYP .GT. 479) IYP = 479
C
C       MAKE A CROSS
```

```
C
        CALL TCPPLT(2,IX,IYM)   !DOWN FROM CENTER
        CALL TCPPLT(2,IX,IYP)   !UP FROM CENTER
        CALL TCPPLT(2,IX,IY)    !TO CENTER
        CALL TCPPLT(2,IXM,IY)   !LEFT FROM CENTER
        CALL TCPPLT(2,IXP,IY)   !RIGHT FROM CENTER
C
C       CONNECT THE ENDS
C
        CALL TCPPLT(2,IX,IYM)
        CALL TCPPLT(2,IXM,IY)
        CALL TCPPLT(2,IX,IYP)
        CALL TCPPLT(2,IXP,IY)
C
        RETURN
        END
        SUBROUTINE   PLTLIN(IXS,IYS,IX,IY,IB1,X,Y)
C
        COMMON /COM002/ ILOG,LR,IYA,XLO,YLO,XHI,YHI,AX,XLN,XSCALE,YLN,YSCALE
C
C
*..............................................................
.....
C       SUBR. STARTS
C
        IF (.NOT. (IXS)) GO TO 100
        XX = X
        IF (ILOG) XX = ALOG10(X)
        IX = INT((XX - AX) * (XLN / XSCALE)) + LR
C
100     IF (.NOT. (IYS)) GO TO 200
        IY = INT((Y - YLO) * (YLN / YSCALE)) + IYA
C
200     IF (IX .LT. 0) IX = 0
        IF (IY .LT. 0) IY = 0
        IF (IY .GT. 479) IY = 479
        CALL TCPPLT(IB1,IX,IY)
C
        RETURN
        END
        SUBROUTINE   RDCNFL(IFUN,IERR,NBRAVG,SPAN,CRIT)
C
        BYTE SETNAM(6)
        BYTE CORFIL(11),GRFILE(11),XFRFIL(16),RTYPE,NFR,PRSW,GRD,SJT,AFT
C
        COMMON /COM001/ CORFIL,GRFILE,XFRFIL,RTYPE,NFR,PRSW,GRD,SJT,AFT
        COMMON /COM003/ DPKHZ,FAKHZ,FAATTN,FBKHZ,FBATTN,DBSPL,STZ,STP,TDB
        COMMON /COM010/ SETNAM
C
```

```
C
*..................................................
*
C      SUBR STARTS
C
       IERR = 0
       GO TO (100,200) IFUN
C
C      ...................................
C      INIT. READ
C
100    READ (2,110) SETNAM
       READ (2,110) SETNAM
110    FORMAT(2X,6A1)
C
       READ (2,120,ERR=130) SETNAM,RATTN,NBRAVG,STP,SPAN,CORFIL,
     +       NFR,CRIT,PRSW,RTYPE,GRFILE,GRD,SJT,AFT
120    FORMAT(2X,6A1,2X,F7.3,1X,I2,1X,F3.1,1X,F5.2,1X,11A1,1X,1A1,
     +   2X,F3.1,3X,1A1,3X,1A1,1X,11A1,3(1X,1A1))
       GO TO 140
C
130    IERR = 1
       RETURN
C
140    READ (2,110) SETNAM
       READ (2,110) SETNAM
       CALL ATTN(1,INT(RATTN))
       CALL ATTN(2,INT(RATTN))
       RETURN
C
C      ...................................
C      DATA READ
C
200    READ (2,210,ERR=220) SETNAM,DPKHZ,FAKHZ,FAATTN,FBKHZ,
     +          FBATTN,DBSPL,STZ,TDB
210    FORMAT (2X,6A1,2X,F7.3,1X,F7.4,1X,F8.2,1X,F7.4,1X,F8.4,
     +      1X,F7.2,1X,F8.1,1X,F8.1)
C
220    IF (SETNAM(1) .EQ. 'S') GO TO 250
       IF (SETNAM(1) .EQ. '_') IERR = 1
       IF (IERR) CALL CLOSE (2)
       RETURN
C
250    BACKSPACE 2
       READ (2,260,ERR=300) SETNAM,RATTN,STP
260    FORMAT(2X,6A1,2X,F7.3,4X,F3.1)
C
       CALL HPCHAN ('B')
       CALL HPATTN (80.0)
       CALL HPFREQ (30.0)
       CALL HPCHAN ('A')
```

```
        CALL HPATTN (80.0)
        CALL HPFREQ (30.0)
        CALL ATTN(1,INT(RATTN))
        CALL ATTN(2,INT(RATTN))
        GO TO 200
C
300     CALL ATTN(1,127)
        CALL ATTN(2,127)
        STOP 'ERROR READING ATTENUATION AND STOP POINT'
        END
        SUBROUTINE  SCFUNC(IFUN,IL,IC)
C
        BYTE CP(8),CS(4),CG(2)
C
        DATA CG /27,12/              !CLEAR GRAPH
        DATA CS /27,'[','2','J'/     !CLEAR SCREEN
        DATA CP /27,'[','0','0',';','0','0','H'/   !POSITION CURSOR
C
C       ............................................................
C       SUBR. STARTS
C
        GO TO (100,200,300) IFUN
C
C       SCREEN CLEAR
C
100     WRITE (5,110) CS
110     FORMAT(1X,4A1)
        RETURN
C
C       CLEAR GRAPH
C
200     WRITE (5,210) 29,CG
210     FORMAT(1X,3A1)
        RETURN
C
C       POSITION CURSOR
C
300     ENCODE (2,310,CP(3)) IL
        ENCODE (2,310,CP(6)) IC
310     FORMAT(I2)
C
        IF (CP(3) .EQ. ' ') CP(3) = '0' !REPLACE SPACE WITH ZERO
        IF (CP(6) .EQ. ' ') CP(6) = '0'
        WRITE (5,320) CP
320     FORMAT(1X,8A1,$)
C
        RETURN
        END
        SUBROUTINE  SNDSET(NBRAVG,SPAN)
C
        BYTE SETNAM(6)
```

```
        BYTE OLDSET(6)      !Previous set-up name, saved.
        BYTE AVGCMD(13)     !"Set number-of-averages" command.
        BYTE CFCMD(16)      !Command to establish the center frequency.
C
        BYTE SETUP(18)
C
        COMMON /COM003/ DPKHZ,FAKHZ,FAATTN,FBKHZ
        COMMON /COM010/ SETNAM,OLDSET
C
C
*****************************************************************
******
C       SUBR. STARTS
C
        DO 10 I = 1,6
        IF (SETNAM(I) .NE. OLDSET(I)) GO TO 20
10      CONTINUE
C
        GO TO 350  !Dont recall same set-up.
C
20      CALL INSERT('DSFN"        ',SETUP,1,18) !ELSE, SETUP THE SETUP
        CALL INSERT(SETNAM,SETUP,6,6)
        DO 23 I = 1,6
        J = I + 5
        SETUP(J) = SETNAM(I)
23      CONTINUE
        IX = INDEX(SETUP,' ')
        CALL INSERT('";RSTA;',SETUP,IX,7)
        J = IBUP (0, 16, SETUP, 18)          !SEND IT
C
C       SEND FREQ. SPAN
C
        ENCODE (16, 110, CFCMD) SPAN * 1000.0 !SETUP THE FREQ. SPAN
110.    FORMAT ('SP ', F9.3, ' Hz;')
        J = IBUP (0, 16, CFCMD, 16)          !SEND IT
        J = IBUP (0, 16, 'FAVD;',5)
C
C       SEND NUMBER AVGS.
C
        ENCODE (13, 300, AVGCMD) NBRAVG      !SET UP # AVGS
300     FORMAT ('NAVG ', I3, ' ENT;')
        J = IBUP (0, 16, AVGCMD, 13)         !SEND IT
C
C       SAVE SETUP
C
        CALL INSERT (SETNAM,OLDSET,1,6)
C
C       SEND CENTER FREQ.
C
350     ENCODE (16, 360, CFCMD) DPKHZ * 1000.0 !MAKE ASCII STRING
360     FORMAT ('CF ', F9.3, ' Hz;')
```

40

```
        J = IBUP (0, 16, CFCMD, 16)        !SEND IT
C
        CALL HPCHAN ('A')          !SELECT CHANNEL A
        CALL HPFREQ (FAKHZ)         !SEND FREQ.
        CALL HPCHAN ('B')          !SAME FOR B
        CALL HPFREQ (FBKHZ)
C
        RETURN
        END
        SUBROUTINE   TCPPLT(IGS,IX,IY)
C
        DIMENSION IPLT(5)
C
        DATA IPLT /29,4*0/
C
C..............................................................
C       SUBROUTINE STARTS
C
C
        ITEMP = (IY * 13) / 8      !Scale to RETROGRAPHICS
        IPLT(2) = (ITEMP / 32) + 32   !1ST Y BYTE
        IPLT(3) = MOD(ITEMP,32) + 96  !2ND Y BYTE
C
        ITEMP = (IX * 8) / 5       !AS ABOVE FOR X'S
        IPLT(4) = (ITEMP / 32) + 32
        IPLT(5) = MOD(ITEMP,32) + 64
C
C       IGS = 1 FOR GS INCLUSION (NO PLOT LINE), OR 2 FOR GS
C       EXCLUSION (DRAW A LINE).
C
        DO 500 I = IGS,5          !SEND FOR GRAPH
        CALL TEKOUT(IPLT(I))
500     CONTINUE
C
        RETURN
        END
```

41

COMMAND FILE TO COMPILE DPOAE

```
R FORTRA
DPOAE=DPOAE/E/W
FILXST=FILXST/E/W
RDCNFL=RDCNFL/E/W
DPPRNT=DPPRNT/E/W
GPFPRM=GPFPRM/E/W
TCPPLT=TCPPLT/E/W
SNDSET=SNDSET/E/W
DPSYN=DPSYN/E/W
DPDSPD=DPDSPD/E/W
DPIOPL=DPIOPL/E/W
DPARPL=DPARPL/E/W
DPPLT1=DPPLT1/E/W
DPPLT2=DPPLT2/E/W
PLTLIN=PLTLIN/E/W
PLTCRS=PLTCRS/E/W
PLAXIS=PLAXIS/E/W
LBLXLG=LBLXLG/E/W
DPNERR=DPNERR/E/W
SCFUNC=SCFUNC/E/W
NSFLRJ=NSFLRJ/E/W
DPPPRM=DPPPRM/E/W
MACTIT=MACTIT/E/W
DPIOEX=DPIOEX/E/W
DPAREX=DPAREX/E/W
DPVERF=DPVERF/E/W
CFRKHZ=CFRKHZ/E/W
DPIOP=DPIOP/E/W
DPARP=DPARP/E/W
DPCDFX=DPCDFX/E/W
```

COMMAND FILE TO LINK DPOAE

```
R LINK
DPOAE=DPOAE,LABLIB//
FILXST
RDCNFL
DPPRNT
GPFPRM
TCPPLT
SNDSET
DPSYN
DPDSPD
DPIOPL
DPARPL
DPPLT1
DPPLT2
PLTLIN
PLTCRS
PLAXIS
LBLXLG
DPNERR
SCFUNC
NSFLRJ
DPPPRM/O:1
MACTIT/O:1
DPIOEX/O:1
DPAREX/O:1
DPVERF/O:2
CFRKHZ/O:2
DPIOP/O:2
DPARP/O:2
DPCDFX/O:3
//
^C
```

DPOAE AUDIOGRAM CONTROL FILE

```
|defaults| attn  |na|stp|winsp|corfile    |nr|cr|op|pr|rt|gr file   |gr dump|
| STOP!  |10.0   | 4|0.0| 1.00|HAOPHE.COR |Y |5.0|N|Y|-|A|HAOPHE.GPF |Y|----|
|--------|-------|--|---|-----|------------|--|---|-|-|-|-|-----------|-|---|
```

| SET-UP | DPkhz | FAkhz | FAattn | FBkhz | FBattn | dBSPL | STEPSZ | MINSPL |
|--------|-------|-------|--------|-------|--------|-------|--------|--------|
| ETP0 | 0.359 | 0.455 | 13.00 | 0.551 | 13.00 | 75.0 | 10.0 | 55.0 |
| ETP0 | 0.508 | 0.643 | 13.00 | 0.778 | 13.00 | 75.0 | 10.0 | 55.0 |
| ETP0 | 0.718 | 0.909 | 13.00 | 1.100 | 13.00 | 75.0 | 10.0 | 55.0 |
| ETP0 | 0.770 | 0.975 | 13.00 | 1.180 | 13.00 | 75.0 | 10.0 | 55.0 |
| ETP0 | 0.826 | 1.045 | 13.00 | 1.264 | 13.00 | 75.0 | 10.0 | 55.0 |
| ETP0 | 0.884 | 1.119 | 13.00 | 1.354 | 13.00 | 75.0 | 10.0 | 55.0 |
| ETP0 | 0.948 | 1.200 | 13.00 | 1.452 | 13.00 | 75.0 | 10.0 | 55.0 |
| ETP0 | 1.015 | 1.285 | 13.00 | 1.555 | 13.00 | 75.0 | 10.0 | 55.0 |
| ETP0 | 1.089 | 1.378 | 13.00 | 1.667 | 13.00 | 75.0 | 10.0 | 55.0 |
| ETP0 | 1.167 | 1.477 | 13.00 | 1.787 | 13.00 | 75.0 | 10.0 | 55.0 |
| ETP0 | 1.251 | 1.583 | 13.00 | 1.915 | 13.00 | 75.0 | 10.0 | 55.0 |
| ETP0 | 1.340 | 1.696 | 13.00 | 2.052 | 13.00 | 75.0 | 10.0 | 55.0 |
| ETP0 | 1.436 | 1.818 | 13.00 | 2.200 | 13.00 | 75.0 | 10.0 | 55.0 |
| ETP0 | 1.540 | 1.949 | 13.00 | 2.358 | 13.00 | 75.0 | 10.0 | 55.0 |
| ETP0 | 1.650 | 2.088 | 13.00 | 2.526 | 13.00 | 75.0 | 10.0 | 55.0 |
| ETP0 | 1.768 | 2.238 | 13.00 | 2.708 | 13.00 | 75.0 | 10.0 | 55.0 |
| ETP0 | 1.895 | 2.399 | 13.00 | 2.903 | 13.00 | 75.0 | 10.0 | 55.0 |
| ETP0 | 2.031 | 2.571 | 13.00 | 3.111 | 13.00 | 75.0 | 10.0 | 55.0 |
| ETP0 | 2.176 | 2.755 | 13.00 | 3.334 | 13.00 | 75.0 | 10.0 | 55.0 |
| ETP0 | 2.334 | 2.954 | 13.00 | 3.574 | 13.00 | 75.0 | 10.0 | 55.0 |
| ETP0 | 2.500 | 3.165 | 13.00 | 3.830 | 13.00 | 75.0 | 10.0 | 55.0 |
| ETP0 | 2.680 | 3.393 | 13.00 | 4.106 | 13.00 | 75.0 | 10.0 | 55.0 |
| ETP0 | 2.872 | 3.636 | 13.00 | 4.400 | 13.00 | 75.0 | 10.0 | 55.0 |
| ETP0 | 3.079 | 3.897 | 13.00 | 4.715 | 13.00 | 75.0 | 10.0 | 55.0 |
| ETP0 | 3.300 | 4.177 | 13.00 | 5.054 | 13.00 | 75.0 | 10.0 | 55.0 |
| ETP0 | 3.537 | 4.477 | 13.00 | 5.417 | 13.00 | 75.0 | 10.0 | 55.0 |
| ETP0 | 3.790 | 4.798 | 13.00 | 5.806 | 13.00 | 75.0 | 10.0 | 55.0 |
| ETP0 | 4.063 | 5.143 | 13.00 | 6.223 | 13.00 | 75.0 | 10.0 | 55.0 |
| ETP0 | 4.354 | 5.512 | 13.00 | 6.670 | 13.00 | 75.0 | 10.0 | 55.0 |
| ETP0 | 4.667 | 5.907 | 13.00 | 7.147 | 13.00 | 75.0 | 10.0 | 55.0 |
| ETP0 | 5.001 | 6.331 | 13.00 | 7.661 | 13.00 | 75.0 | 10.0 | 55.0 |
| ETP0 | 5.360 | 6.785 | 13.00 | 8.210 | 13.00 | 75.0 | 10.0 | 55.0 |
| ETP0 | 5.746 | 7.273 | 13.00 | 8.800 | 13.00 | 75.0 | 10.0 | 55.0 |

CORRECTION FILE FOR DPOAE AMPLITUDE

| | |
|---|---|
| 0.500 | 4.11 |
| 0.707 | 3.46 |
| 1.000 | 1.43 |
| 1.072 | 0.46 |
| 1.149 | 0.25 |
| 1.231 | -0.01 |
| 1.320 | -0.01 |
| 1.414 | -0.17 |
| 1.516 | -0.36 |
| 1.625 | -0.52 |
| 1.741 | -0.87 |
| 1.866 | -0.87 |
| 2.000 | -0.75 |
| 2.144 | -0.40 |
| 2.297 | 0.29 |
| 2.462 | 0.46 |
| 2.639 | 0.81 |
| 2.828 | 1.31 |
| 3.031 | 2.19 |
| 3.249 | 2.60 |
| 3.482 | 3.05 |
| 3.732 | 3.56 |
| 4.000 | 4.13 |
| 4.287 | 4.61 |
| 4.595 | 5.55 |
| 4.925 | 6.44 |
| 5.278 | 8.23 |
| 5.657 | 9.51 |
| 6.063 | 10.36 |
| 6.498 | 10.48 |
| 6.964 | 9.24 |
| 7.464 | 6.92 |
| 8.000 | 5.32 |
| 999.00 | 0.00 |

AUDIOGRAM GRAPH PARAMETER FILE

Y
  500.
  8000.
  -20.
  30.
  5.
  10.
  1.04    14.78
  1.18    14.7
  1.32    14.8
  1.46    14.62
  1.60    13.88
  1.74    13.40
  1.88    13.19
  2.02    12.6
  2.16    12.34
  2.30    11.60
  2.43    11.60
  2.57    10.91
  2.71    11.3
  2.85    11.8
  2.99    12.97
  3.13    13.67
  3.27    14.53
  3.41    15.1
  3.55    15.74
  3.69    16.57
  3.83    17.29
  3.96    17.95
  4.10    18.56
  4.24    19.28
  4.38    19.97
  4.52    20.89
  4.66    21.59
  4.80    22.42
  4.94    22.95
  5.08    23.59
  5.22    24.16
  5.36    24.74
  5.49    25.1
  5.63    25.5
  5.77    25.79
  5.91    25.95
  6.05    25.99
  6.19    25.66
  6.33    25.50
  6.47    25.30
  6.61    24.99

| | |
|---|---|
| 6.75 | 24.3 |
| 6.89 | 23.56 |
| 7.02 | 22.77 |
| 7.16 | 22.21 |
| 7.30 | 21.60 |
| 7.44 | 21.02 |
| 7.58 | 20.44 |
| 7.72 | 19.89 |
| 7.86 | 19.4 |
| 8.00 | 19.27 |
| 999.00 | 0.00 |
| 75 AUD AV + STD | |
| 1.04 | 3.95 |
| 1.18 | 4.79 |
| 1.32 | 5.08 |
| 1.46 | 5.26 |
| 1.60 | 4.88 |
| 1.74 | 5.02 |
| 1.88 | 4.8 |
| 2.02 | 4.6 |
| 2.16 | 3.93 |
| 2.30 | 3.70 |
| 2.43 | 2.85 |
| 2.57 | 2.84 |
| 2.71 | 2.91 |
| 2.85 | 3.38 |
| 2.99 | 3.87 |
| 3.13 | 4.57 |
| 3.27 | 5.44 |
| 3.41 | 6.18 |
| 3.55 | 6.85 |
| 3.69 | 7.48 |
| 3.83 | 8.2 |
| 3.96 | 9.13 |
| 4.10 | 9.91 |
| 4.24 | 10.6 |
| 4.38 | 11. |
| 4.52 | 11.9 |
| 4.66 | 12.3 |
| 4.80 | 12.7 |
| 4.94 | 13.3 |
| 5.08 | 13.8 |
| 5.22 | 14.4 |
| 5.36 | 14. |
| 5.49 | 15.1 |
| 5.63 | 15.0 |
| 5.77 | 15.1 |
| 5.91 | 15.2 |
| 6.05 | 15.1 |
| 6.19 | 14.6 |
| 6.33 | 14.3 |

| | |
|---|---|
| 6.47 | 13.8 |
| 6.61 | 13.3 |
| 6.75 | 12.5 |
| 6.89 | 11.8 |
| 7.02 | 11.0 |
| 7.16 | 10.6 |
| 7.30 | 10.0 |
| 7.44 | 9.44 |
| 7.58 | 8.63 |
| 7.72 | 7.8 |
| 7.86 | 7.40 |
| 8.00 | 6.38 |
| 999.00 | 0.00 |
| 75 AUD AV - STD | |
| 1.04 | 2.196 |
| 1.18 | -0.27 |
| 1.32 | -1.09 |
| 1.46 | -2.27 |
| 1.60 | -3.42 |
| 1.74 | -4.49 |
| 1.88 | -4.8 |
| 2.02 | -4.96 |
| 2.16 | -4.98 |
| 2.30 | -5.27 |
| 2.43 | -5.37 |
| 2.57 | -5.73 |
| 2.71 | -5.50 |
| 2.85 | -5.48 |
| 2.99 | -5.65 |
| 3.13 | -5.96 |
| 3.27 | -6.4 |
| 3.41 | -6.65 |
| 3.55 | -6.90 |
| 3.69 | -7.20 |
| 3.83 | -7.26 |
| 3.96 | -7.34 |
| 4.10 | -7.03 |
| 4.24 | -6.89 |
| 4.38 | -6.56 |
| 4.52 | -6.28 |
| 4.66 | -5.45 |
| 4.80 | -4. |
| 4.94 | -3.35 |
| 5.08 | -1.94 |
| 5.22 | -0.78 |
| 5.36 | 0.630 |
| 5.49 | 1.456 |
| 5.63 | 2.326 |
| 5.77 | 2.946 |
| 5.91 | 3.864 |
| 6.05 | 4.504 |

48

| | |
|---|---|
| 6.19 | 4.924 |
| 6.33 | 5.194 |
| 6.47 | 5.575 |
| 6.61 | 6.007 |
| 6.75 | 6.298 |
| 6.89 | 6.07 |
| 7.02 | 5.502 |
| 7.16 | 4.853 |
| 7.30 | 4.137 |
| 7.44 | 3.588 |
| 7.58 | 2.821 |
| 7.72 | 2.127 |
| 7.86 | 1.354 |
| 8.00 | 0.754 |
| 999.00 | 0.00 |

AV AUD 75 NF + STD

| | |
|---|---|
| 1.04 | -4.514 |
| 1.18 | -4.436 |
| 1.32 | -5.682 |
| 1.46 | -6.738 |
| 1.60 | -7.372 |
| 1.74 | -7.849 |
| 1.88 | -8.410 |
| 2.02 | -8.920 |
| 2.16 | -9.217 |
| 2.30 | -9.337 |
| 2.43 | -9.378 |
| 2.57 | -9.73 |
| 2.71 | -10.03 |
| 2.85 | -10.34 |
| 2.99 | -10.34 |
| 3.13 | -10.54 |
| 3.27 | -10.54 |
| 3.41 | -10.7 |
| 3.55 | -10.81 |
| 3.69 | -10.59 |
| 3.83 | -10.74 |
| 3.96 | -11.08 |
| 4.10 | -11.08 |
| 4.24 | -11.11 |
| 4.38 | -10.74 |
| 4.52 | -10.93 |
| 4.66 | -10.77 |
| 4.80 | -10.52 |
| 4.94 | -9.462 |
| 5.08 | -8.1 |
| 5.22 | -7.411 |
| 5.36 | -7.050 |
| 5.49 | -6.652 |
| 5.63 | -5.810 |
| 5.77 | -4.346 |

| | |
|---|---|
| 5.91 | -3.340 |
| 6.05 | -2.302 |
| 6.19 | -1.833 |
| 6.33 | -1.248 |
| 6.47 | -0.993 |
| 6.61 | -0.73 |
| 6.75 | -0.329 |
| 6.89 | -0.469 |
| 7.02 | -0.32 |
| 7.16 | -0.78 |
| 7.30 | -0.836 |
| 7.44 | -1.492 |
| 7.58 | -2.270 |
| 7.72 | -2.855 |
| 7.86 | -3.337 |
| 8.00 | -3.678 |
| 999.00 | 0.00 |

AV AUD 75 NF - STD

| | |
|---|---|
| 1.04 | 9.45 |
| 1.18 | 10.5 |
| 1.32 | 11.7 |
| 1.46 | 11. |
| 1.60 | 10.5 |
| 1.74 | 9.47 |
| 1.88 | 8.28 |
| 2.02 | 7.60 |
| 2.16 | 6.92 |
| 2.30 | 6.17 |
| 2.43 | 5.4 |
| 2.57 | 5.08 |
| 2.71 | 5.15 |
| 2.85 | 5.65 |
| 2.99 | 6.18 |
| 3.13 | 6.85 |
| 3.27 | 7.63 |
| 3.41 | 8.53 |
| 3.55 | 9.77 |
| 3.69 | 10.8 |
| 3.83 | 11.6 |
| 3.96 | 12.3 |
| 4.10 | 13.1 |
| 4.24 | 13.9 |
| 4.38 | 14.8 |
| 4.52 | 15.7 |
| 4.66 | 16. |
| 4.80 | 17.3 |
| 4.94 | 17.9 |
| 5.08 | 18.5 |
| 5.22 | 18.9 |
| 5.36 | 19.5 |
| 5.49 | 19.6 |

| | |
|---:|---:|
| 5.36 | 5.6589 |
| 5.49 | 5.6530 |
| 5.63 | 5.0716 |
| 5.77 | 4.8986 |
| 5.91 | 4.6311 |
| 6.05 | 4.804 |
| 6.19 | 4.0090 |
| 6.33 | 3.3736 |
| 6.47 | 2.5728 |
| 6.61 | 2.2029 |
| 6.75 | 1.4426 |
| 6.89 | 1.0397 |
| 7.02 | 0.2947 |
| 7.16 | 0.1106 |
| 7.30 | -0.383 |
| 7.44 | -0.753 |
| 7.58 | -1.134 |
| 7.72 | -1.806 |
| 7.86 | -2.064 |
| 8.00 | -2.258 |
| 999.00 | 0.00 |

AV AUD 65 - STD

| | |
|---:|---:|
| 1.04 | -1.7046 |
| 1.18 | -3.6785 |
| 1.32 | -5.1266 |
| 1.46 | -6.524 |
| 1.60 | -7.7620 |
| 1.74 | -8.9302 |
| 1.88 | -9.2837 |
| 2.02 | -9.0237 |
| 2.16 | -8.6558 |
| 2.30 | -9.2944 |
| 2.43 | -9.736 |
| 2.57 | -10.202 |
| 2.71 | -10.160 |
| 2.85 | -9.9322 |
| 2.99 | -9.9010 |
| 3.13 | -10.145 |
| 3.27 | -10.20 |
| 3.41 | -10.475 |
| 3.55 | -9.9642 |
| 3.69 | -9.7440 |
| 3.83 | -9.5724 |
| 3.96 | -10.373 |
| 4.10 | -10.9 |
| 4.24 | -11.172 |
| 4.38 | -11.000 |
| 4.52 | -10.433 |
| 4.66 | -10.178 |
| 4.80 | -9.7236 |
| 4.94 | -9.5813 |

| | |
|---|---|
| 5.63 | 19. |
| 5.77 | 19.7 |
| 5.91 | 19.9 |
| 6.05 | 19.9 |
| 6.19 | 19.8 |
| 6.33 | 19.3 |
| 6.47 | 19.1 |
| 6.61 | 18.8 |
| 6.75 | 18.3 |
| 6.89 | 17.6 |
| 7.02 | 17.0 |
| 7.16 | 16.3 |
| 7.30 | 15.5 |
| 7.44 | 14.5 |
| 7.58 | 13.9 |
| 7.72 | 13.2 |
| 7.86 | 12.7 |
| 8.00 | 12.2 |
| 999.00 | 0.00 |

65 AUD AV + STD

| | |
|---|---|
| 1.04 | 1.8420 |
| 1.18 | 1.8145 |
| 1.32 | 1.162 |
| 1.46 | 0.3147 |
| 1.60 | -0.569 |
| 1.74 | -1.6 |
| 1.88 | -2.25 |
| 2.02 | -3.022 |
| 2.16 | -3.896 |
| 2.30 | -5.14 |
| 2.43 | -5.77 |
| 2.57 | -6.138 |
| 2.71 | -5.923 |
| 2.85 | -5.086 |
| 2.99 | -4.400 |
| 3.13 | -3.662 |
| 3.27 | -2.932 |
| 3.41 | -2.361 |
| 3.55 | -1.310 |
| 3.69 | -0.637 |
| 3.83 | 0.3586 |
| 3.96 | 0.9347 |
| 4.10 | 1.4888 |
| 4.24 | 2.1902 |
| 4.38 | 2.5201 |
| 4.52 | 3.1214 |
| 4.66 | 3.7868 |
| 4.80 | 4.4896 |
| 4.94 | 5.1108 |
| 5.08 | 5.2629 |
| 5.22 | 5.5657 |

52.

| | |
|---|---|
| 5.08 | -8.8902 |
| 5.22 | -8.1826 |
| 5.36 | -7.3070 |
| 5.49 | -6.754 |
| 5.63 | -6.0291 |
| 5.77 | -5.3078 |
| 5.91 | -4.7311 |
| 6.05 | -4.2696 |
| 6.19 | -3.9666 |
| 6.33 | -3.2263 |
| 6.47 | -2.6605 |
| 6.61 | -2.6382 |
| 6.75 | -2.6249 |
| 6.89 | -2.7753 |
| 7.02 | -2.9708 |
| 7.16 | -3.3507 |
| 7.30 | -4.0275 |
| 7.44 | -4.7458 |
| 7.58 | -5.2700 |
| 7.72 | -5.9322 |
| 7.86 | -6.611 |
| 8.00 | -6.4885 |
| 999.00 | 0.00 |

AV AUD 65 NF + STD

| | |
|---|---|
| 1.04 | -9.193 |
| 1.18 | -8.778 |
| 1.32 | -9.883 |
| 1.46 | -11.54 |
| 1.60 | -12.60 |
| 1.74 | -12. |
| 1.88 | -12.91 |
| 2.02 | -13.49 |
| 2.16 | -14.10 |
| 2.30 | -14.43 |
| 2.43 | -14.31 |
| 2.57 | -13.86 |
| 2.71 | -13.55 |
| 2.85 | -13.69 |
| 2.99 | -13.53 |
| 3.13 | -13.71 |
| 3.27 | -13.57 |
| 3.41 | -13.73 |
| 3.55 | -13.66 |
| 3.69 | -13.74 |
| 3.83 | -13.68 |
| 3.96 | -13.53 |
| 4.10 | -13.68 |
| 4.24 | -13.68 |
| 4.38 | -13.61 |
| 4.52 | -13.42 |
| 4.66 | -13.04 |

| | |
|---|---|
| 4.80 | -12.8 |
| 4.94 | -12.40 |
| 5.08 | -11.93 |
| 5.22 | -11.20 |
| 5.36 | -10.54 |
| 5.49 | -10.09 |
| 5.63 | -9.753 |
| 5.77 | -9.066 |
| 5.91 | -8.426 |
| 6.05 | -7.814 |
| 6.19 | -7.370 |
| 6.33 | -7.260 |
| 6.47 | -7.166 |
| 6.61 | -7.017 |
| 6.75 | -6.845 |
| 6.89 | -6.773 |
| 7.02 | -7.064 |
| 7.16 | -7.736 |
| 7.30 | -8.499 |
| 7.44 | -8.863 |
| 7.58 | -9.288 |
| 7.72 | -9.498 |
| 7.86 | -9.852 |
| 8.00 | -11.15 |
| 999.00 | 0.00 |

AV AUD 65 NF - STD

| | |
|---|---|
| 0.999 | 8.82 |
| 1.230 | 8.43 |
| 1.513 | 5.73 |
| 1.863 | 4.16 |
| 2.292 | 3.92 |
| 2.822 | 3.56 |
| 3.475 | 4.95 |
| 4.277 | 8.60 |
| 5.265 | 11.24 |
| 6.482 | 9.79 |
| 7.980 | 2.40 |
| 999.00 | 0.00 |

AV AUD 55 + STD

| | |
|---|---|
| 0.999 | -2.18 |
| 1.230 | -1.18 |
| 1.513 | -4.58 |
| 1.863 | -6.43 |
| 2.292 | -11.14 |
| 2.822 | -8.32 |
| 3.475 | -7.76 |
| 4.277 | -5.08 |
| 5.265 | -1.36 |
| 6.482 | -2.03 |

```
 7.980   -7.34
999.00    0.00
AV AUD 55 - STD 0.999    2.47
 1.230    0.87
 1.513   -7.98
 1.863   -9.63
 2.292  -10.70
 2.822   -5.75
 3.475   -9.44
 4.277  -12.60
 5.265  -10.19
 6.482   -5.91
 7.980  -10.25
999.00    0.00
AV AUD 55 NF + STD 0.999   -9.40
 1.230  -10.73
 1.513  -13.92
 1.863  -15.62
 2.292  -15.32
 2.822  -16.26
 3.475  -15.05
 4.277  -15.30
 5.265  -12.40
 6.482  -10.36
 7.980  -13.23
999.00    0.00
AV AUD 55 + STD
```

I/O CONTROL FILE

```
|defaults| attn  |na|stp|winsp|corfile    |nr|cr|op|pr|rt|gr file   |gr dump|
| STOP|  |10.0   | 4|3.0| 1.00|HIAPHE.COR |Y |5.0|N|Y|-|I|HIAPHE.GPF |Y|-----|
|--------|-------|--|---|-----|------------|--|---|-|-|-|-|-----------|-|---
- -|
| SET-UP | DPkhz | FAkhz | FAattn | FBkhz | FBattn | dBSPL | STEPSZ | MINSPL |
| ETP0   | 0.359 | 0.455 |  3.00  | 0.551 |  3.00  |  85.0 |  5.0   |  25.0  |
| ETP0   | 0.718 | 0.909 |  3.00  | 1.100 |  3.00  |  85.0 |  5.0   |  25.0  |
| ETP0   | 1.436 | 1.818 |  3.00  | 2.200 |  3.00  |  85.0 |  5.0   |  25.0  |
| ETP0   | 2.154 | 2.727 |  3.00  | 3.300 |  3.00  |  85.0 |  5.0   |  25.0  |
| ETP0   | 2.872 | 3.636 |  3.00  | 4.400 |  3.00  |  85.0 |  5.0   |  25.0  |
| STOP|  |10.0   | 4|0.0||        |        |       |        |        |
| ETP0   | 4.309 | 5.455 |  3.00  | 6.601 |  3.00  |  85.0 |  5.0   |  25.0  |
| ETP0   | 5.746 | 7.273 |  3.00  | 8.800 |  3.00  |  85.0 |  5.0   |  25.0  |
|_____|_____|_____|_____|_____|_____|_____|_____|_____|___
_____|
```

I/O CORRECTION FILE

| | |
|---|---|
| 0.50 | 4.11 |
| 1.00 | 1.43 |
| 2.00 | -0.75 |
| 3.00 | 2.19 |
| 4.00 | 4.13 |
| 6.00 | 10.32 |
| 8.00 | 5.32 |
| 999.00 | 0.00 |

I/O GRAPH PARAMETER FILE

N
25.
85.
-20.
30.
1.
10.
1.
10.

What is claimed is:

1. Apparatus for distortion product emission audiogram testing of a human being comprising, signal generating means for generating a first electrical signal of frequency $f_1$ and a second electrical signal of frequency $f_2$, the frequency $f_2$ being greater than the frequency $f_1$, first and second earphones responsive respectively to said first and second electrical signals for producing a first tone of frequency $f_1$ and a second tone of frequency $f_2$, an eartip adapted for insertion in the ear canal of the outer ear of said human being, said eartip having first and second audio tubes terminated therein which are connected respectively to said first and second earphones which transmit said first tone and said second tone to said ear, said eartip including a microphone with a first output lead connected thereto, signal analyzing means responsive to said first output lead connected to said microphone for generating a signal corresponding to a level of a tone generated in the ear of said human being at a frequency of $2f_1-f_2$, digital computer means for controlling said signal generating means to produce a plurality of sets of signals of frequency $f_1$ and $f_2$ where the ratio of such frequencies $f_2/f_1$ is approximately the same for each set of signals, and responsive to said signal analyzing means for recording each level of said tone at frequency of $2f_1-f_2$ corresponding to each of said sets of frequencies $f_1$, $f_2$, and plotting means responsive to said digital computer means having stored therein tone levels at frequencies of $2f_1-f_2$ for plotting said levels of each of said tones at frequency of $2f_1-f_2$ as a function of frequency equal to the geometric mean of the frequencies $f_1$ and $f_2$.

2. A method for reducing noise in distortion product emission testing comprising the steps of:

generating a steady state electrical signal representative of the distortion product emission (DPE) tone from an ear, said DPE tone being of constant amplitude, frequency and phase, said steady state electrical signal being contaminated by random phase noise, repeatedly initiating a time sample having a length which does not drift with respect to the period of said DPE tone to produce a plurality of time samples, and applying said plurality of time samples to a Fourier-transform spectrum analyzer to determine an averaged spectrum to determine the amplitude level of said DPE tone, whereby noise is reduced.

3. A method for reducing noise in distortion product emission testing comprising the steps of generating a first steady state oscillating signal of frequency $f_1$ and a second steady state oscillating signal of frequency $f_2$ and a triggering signal of frequency $2f_1-f_2$ such that said first signal, said second signal and said triggering signal have substantially no phase drift among any of such signals, applying said first steady state oscillating signal of frequency $f_1$ and said second steady state oscillating signal of frequency $f_2$ to the ear canal of the outer ear of a human being, generating a steady state electrical response signal representative of the distortion product emission tone (DPE) of substantially constant amplitude and phase of frequency $2f_1-f_2$ which is generated in the ear in response to said first and second signals, said steady state electrical response signal being contaminated by random phase noise, dividing said steady state electrical response signal by reference to said triggering signal into a plurality of equal length time segment DPE signals such that each DPE signal of frequency $2f_1-f_2$ begins with the same phase, and applying a predetermined number of said equal length time segments to a Fourier-transform spectrum analyzer to determine the amplitude level versus DPE frequency averaged spectrum, whereby said amplitude at said frequency $2f_1-f_2$ of said averaged spectrum substantially represents the level of said DPE tone and the noise level is substantially reduced.

* * * * *